(12) United States Patent
Sansom et al.

(10) Patent No.: US 8,846,143 B2
(45) Date of Patent: *Sep. 30, 2014

(54) METHOD FOR SELECTIVELY ANCHORING AND EXPOSING LARGE NUMBERS OF NANOSCALE STRUCTURES

(75) Inventors: Elijah Bodhi Sansom, San Francisco, CA (US); Derek Rinderknecht, Arcadia, CA (US); Morteza Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 541 days.

This patent is subject to a terminal disclaimer.

(21) Appl. No.: 13/110,877

(22) Filed: May 18, 2011

(65) Prior Publication Data

US 2012/0021164 A1    Jan. 26, 2012

Related U.S. Application Data

(63) Continuation-in-part of application No. 11/827,169, filed on Jul. 10, 2007, now Pat. No. 7,955,644.

(60) Provisional application No. 60/819,872, filed on Jul. 10, 2006.

(51) Int. Cl.
| | |
|---|---|
| *B05D 7/00* | (2006.01) |
| *B05D 1/38* | (2006.01) |
| *C01B 31/02* | (2006.01) |
| *B82Y 30/00* | (2011.01) |
| *B82Y 40/00* | (2011.01) |
| *B29C 70/64* | (2006.01) |
| *B82B 3/00* | (2006.01) |

(52) U.S. Cl.
CPC ............ *B29C 70/64* (2013.01); *C01B 31/0293* (2013.01); *B82Y 30/00* (2013.01); *B82Y 40/00* (2013.01); *C01B 2202/08* (2013.01); *C01B 31/0253* (2013.01); *C01B 31/0273* (2013.01); *B82B 3/0047* (2013.01); *B82B 3/0014* (2013.01); *B09K 2105/162* (2013.01); *Y10S 977/742* (2013.01); *Y10S 977/753* (2013.01)
USPC ........... 427/214; 427/240; 427/284; 977/742; 977/753

(58) Field of Classification Search
USPC ................... 977/734–753, 762–787; 423/445 R–445 B; 427/180, 202, 203, 427/214, 215, 258, 372.2, 384–387, 402, 427/407.1
See application file for complete search history.

(56) References Cited

U.S. PATENT DOCUMENTS

| | | | |
|---|---|---|---|
| 6,924,335 B2 | 8/2005 | Fan et al. | |
| 7,037,562 B2 | 5/2006 | Jimenez | |
| 7,160,620 B2 | 1/2007 | Huang et al. | |
| 7,183,003 B2 | 2/2007 | Leu et al. | |
| 7,235,442 B2 | 6/2007 | Wang et al. | |
| 7,291,396 B2 | 11/2007 | Huang et al. | |
| 7,393,428 B2 | 7/2008 | Huang et al. | |
| 7,396,477 B2 | 7/2008 | Hsiao | |
| 7,438,844 B2 | 10/2008 | Huang et al. | |
| 7,491,628 B2 | 2/2009 | Noca et al. | |
| 7,569,425 B2 | 8/2009 | Huang et al. | |
| 7,611,628 B1 * | 11/2009 | Hinds, III | 210/500.27 |
| 7,611,651 B2 | 11/2009 | Huang et al. | |
| 7,695,769 B2 * | 4/2010 | Watanabe et al. | 427/372.2 |
| 2005/0127351 A1 | 6/2005 | Tolt | |
| 2005/0136248 A1 | 6/2005 | Leu et al. | |
| 2005/0167647 A1 | 8/2005 | Huang et al. | |
| 2005/0230082 A1 | 10/2005 | Chen | |
| 2005/0245659 A1 | 11/2005 | Chen | |
| 2006/0073332 A1 | 4/2006 | Huang et al. | |
| 2006/0073712 A1 | 4/2006 | Suhir | |
| 2006/0093642 A1 | 5/2006 | Ranade | |
| 2006/0118791 A1 | 6/2006 | Leu et al. | |
| 2006/0231970 A1 | 10/2006 | Huang et al. | |
| 2007/0004081 A1 | 1/2007 | Hsiao | |
| 2007/0059864 A1 | 3/2007 | Huang et al. | |

(Continued)

FOREIGN PATENT DOCUMENTS

| | | |
|---|---|---|
| JP | 2006 114265 | 4/2006 |
| JP | 2006 164835 | 6/2006 |

(Continued)

OTHER PUBLICATIONS

Jung, Yung Joon, et al., "Aligned carbon nanotube-polymer hybrid architectures for diverse flexible electronic applications," Nano Letters, 2006, vol. 6, No. 3, pp. 413-418.
Sansom, Elijah B., et al., "Controlled partial embedding of carbon nanotubes within flexible transparent layers," Nanotechnology, 2008, vol. 19, 035302.
PCT International Preliminary Report on Patentability and The Written Opinion of the International Searching Authority for PCT/US2012/000250, Nov. 19, 2013.
PCT International Preliminary Report on Patentability for PCT/US2010/000243, Aug. 2, 2011.

(Continued)

*Primary Examiner* — William Phillip Fletcher, III
(74) *Attorney, Agent, or Firm* — Mark Stirrat; One LLP

(57) ABSTRACT

Methods for fastening nanoscale structures within an anchoring structure to form a nanostructure composite and nanostructure composites formed therefrom. A primary fluid layer is formed on an anchoring substrate. Nanostructures are provided on an initial substrate, the nanostructures having a defined height and orientation with respect to the initial substrate. The nanostructures are introduced to a desired depth in the primary fluid layer, such that the orientation of the nanostructures relative to the growth substrate is substantially maintained. The primary fluid layer comprises one or more fluid layers. Ones of multiple fluid layers are selected such that when altered to form an anchoring structure, a portion of the anchoring structure can be removed, permitting exposure of at least a portion of the nanostructures from the anchoring structure in which they are affixed. The growth substrate is removed. Ends or other parts of nanostructures may be exposed from the anchoring structure.

27 Claims, 18 Drawing Sheets

(56) References Cited

U.S. PATENT DOCUMENTS

| | | | |
|---|---|---|---|
| 2007/0099311 | A1 | 5/2007 | Zhou et al. |
| 2007/0207182 | A1 | 9/2007 | Weber et al. |
| 2008/0081176 | A1 | 4/2008 | Huang et al. |
| 2008/0145616 | A1 | 6/2008 | Gharib et al. |
| 2009/0032496 | A1 | 2/2009 | Yao et al. |
| 2010/0075024 | A1 | 3/2010 | Ajayan et al. |
| 2010/0253375 | A1 | 10/2010 | Fang et al. |

FOREIGN PATENT DOCUMENTS

| | | |
|---|---|---|
| TW | 253 898 | 4/2006 |
| TW | 256 877 | 6/2006 |
| WO | WO 2006/041535 | 4/2006 |

OTHER PUBLICATIONS

Barber, A. H., et al., "Static and dynamic wetting measurements of single carbon nanotubes," Physical review letters 92(18): 186103, 2004.

Correa-Duarte, M.A., et al., "Nanoengineered polymeric thin films by sintering CNT-coated polystyrene spheres," Small 2 (2): 220-224, 2006.

Firowska, I.O., et al., "Highly ordered MWNT-based matrixes: topography at the nanoscale conceived for tissue engineering," Langmuir 22(12): 5427-5434, 2006.

Jung, Y.J., et al., "Aligned carbon nanotube-polymer hybrid architectures for diverse flexible electronic applications," Nano letters 6(3): 413-418, 2006.

Lahiff, E., et al., "Selective positioning and density control of nanotubes within a polymer thin film," Nano letters 3(10): 1333-1337, 2003.

Mamedov, A. A., et al., "Molecular design of strong single-wall carbon nanotube/polyelectrolyte multilayer composites," Nature materials 1(3): 190-194, 2005.

Melechko, A. V., et al., "Vertically aligned carbon nanofibers and related structures: Controlled synthesis and directed assembly," Journal of applied physics 97(4): 041301, 2005.

Morjan, R.E., et al., "High growth rates and wall decoration of carbon nanotubes grown by plasma-enhanced chemical vapour deposition," Chemical physics letters 383 (3-4): 385-390, 2004.

Ren, Z.F., et al., "Synthesis of large arrays of well-aligned carbon nanotubes on glass," Science 282(5391): 1105-1107, 1998.

Xie, X.L., et al., "Dispersion and alignment of carbon nanotuybes in polymer matrix: A review," materials science & engineering. R, Reports 49(4): 89-112, 2005.

Ajayan, P.M. et al., "Aligned carbon nanotube arrays formed by cutting a polymer resin-nanotube composite," Science 265(5176): 1212-1214, 1994.

Boo, H., et al., "Electrochemical nanoneedle biosensor based on multiwall carbon nanotube," Analytical chemistry 78 (2): 617-620, 2006.

Huber, C.A., et al., "Nanowire array composites," Science 263(5148): 800-802, 1994.

Jin, L., et al., "Alignment of carbon nanotubes in a polymer matrix by mechanical stretching," Applied physics letters 73(9): 1197-1199, 1998.

Li, W. Z., et al., "Large-scale synthesis of aligned carbon nanotubes," Science 274(5293): 1701-1703, 1996.

Ravikar, N. R., et al., "Embedded carbon-nanotube-stiffened polymer surfaces," Small 1(3): 317-320, 2005.

Suh, J.S., and Lee, J.S., "Highly ordered two-dimensional carbon nanotube arrays," Applied physics letters 75(14): 2047-2049, 1999.

Wagner, H.D., et al., "Stress-induced fragmentation of multiwall carbon nanotubes in a polymer matrix," Applied physics letters 72(2): 188-190, 1998.

Wong, E.W., et al., "Nanobeam mechanics: Elasticity, strength, and toughness of nanorods and nanotubes," Science 277(5334): 1971-1975, 1997.

Zhao, L.L., et al., "Porous silicon and alumina as chemically reactive templates for the synthesis of tubes and wires of SnSe, Sn, and $SnO_2$," Angewandle Chemie 45(2): 311-315, 2006.

Nerushev, O.A., et al., "The temperature dedpendence of Fe-catalysed growth of carbon nanotubes on silicon substrates," Physica. B. Condensed matter 323(1-4): 51-59, 2002.

Huang, X., et al., "Inherent-opening-controlled pattern formation in carbon nanotube arrays," Nanotechnology 18 (2007) 305301 (6pp).

Sansom, E.B., "Experimental Investigation on Patterning of Anchored and Unanchored Aligned Carbon Nanotube Mats by Fluid Immersion and Evaporation," Ph. D. Thesis, California Institute of Technology, Pasadena, California, 2007.

PCT International Search Report and the Written Opinion of the International Searching Authority for PCT/US2007/015754, Feb. 2, 2010.

PCT International Preliminary Report on Patentability for PCT/US2007/015754, Feb. 2, 2010.

PCT International Preliminary Report on Patentability for PCT/US2008/012641, May 11, 2010.

Borca-Tasciuc, T., Mazumder, M., Son, Y., Pal, S. K., Schadler, L. S. and Ajayan, P. M., 2007, "Anisotropic thermal diffusivity characterization of aligned carbon nanotube-polymer composites," Journal of Nanoscience and Nanotechnology 7(4): 1581-1588.

Choi, T., Poulikakos, D., Tharian, J. and Sennhauser, U., 2005, "Measurement of thermal conductivity of individual multiwalled carbon nanotubes by the 3-omega method," Applied physics letters 87(1): 013108.

Crabtree, G. W. and Lewis, N. S., 2007, "Solar energy conversion," Physics today 60(3): 37-42.

Falvo, M. R., Clary, G. J., Taylor, R. M., Chi, V., Brooks, F. P., Washburn, S. and Superfine, R., 1997, "Bending and buckling of carbon nanotubes under large strain," Nature 389(6651): 582-584.

Fan, S. S., Chapline, M. G., Franklin, N. R., Tombler, T. W., Cassell, A. M. and Dai, H. J., 1999, "Self-oriented regular arrays of carbon nanotubes and their field emission properties," Science 283(5401): 512-4.

Frank, S., Poncharal, P., Wang, Z. L. and de Heer, W. A., 1998, "Carbon nanotube quantum resistors," Science 280 (5370): 1744-1746.

Hinds, B. J., Chopra, N., Rantell, T., Andrews, R., Gavalas, V. and Bachas, L. G., 2004, "Aligned multiwalled carbon nanotube membranes," Science 303(5654): 62-5.

Huang, H., Liu, C. H., We, Y. and Fan, S. S., 2005, "Aligned carbon nanotube composite films for thermal management," Advanced materials 17(13): 1652.

Iijima, S., 1991, "Helical microtubules of graphitic carbon," Nature 354(6348): 56-58.

Kam, N. W. S., O'Connell, M., Wisdon, J. A. and Dai, H. J., 2005. "Carbon nanotures as multifunctional biological transporters and near-infrared agents for selective cancer cell destruction," Proceedings of the National Academy of Sciences of the United States of America 102(33): 11600-11605.

Kim, P., Shi, L., Majumdar, A. and McEuen, P. L., 2001, "Thermal transport measurements of individual multiwalled nanotubes," Physical review letters 87(21): 215502.

Lee, J. U., 2005, "Photovoltaic effect in ideal carbon nanotube diodes," Applied physics letters 87(7): 073101.

Noca, F., Bronikowski, M., Sansom, E. B., Zhou, J. and Gharibm M., 2007, "Nanowicks," NASA Tech Briefs 31(10): 32-3.

Raravikar, N. R., Schadler, L. S., Vijayaraghavan, A. S., Zhao, Y. P., Wei, B. Q. and Ajayan, P. M., 2005, "Synthesis and characterization of thickness-aligned carbon nanotube-polymer composite films," Chemistry of materials 17(5): 974-983.

Tian, B. Z., Zheng, X. L., Kempa, T. J., Fang, Y., Yu, N. F., Yu, G. H., Huang, J. L. and Lieber, C. M., 2007, "Coaxial silicon nanowires as solar cells and nanoelectronic power sources," Nature 449(7164): 885-8.

Xu, Z., Bai, X. D., Wang, Z. L., and Wang, E. G., 2006, "Multiwall carbon nanotubes made of monochirality graphite shells," Journal of the American Chemical Society 128(4): 1052-1053.

Yurdumakan, B., Raravikar, N. R., Ajayan, P. M., and Dhinojwala, A., 2005, "Synthetic gecko foot-hairs from multiwalled carbon nanotubes," Chemical Communications 30: 3799-3801.

Zhou, J., Noca, F. and Ghanb, M., 2006, "Flow conveying and diagnosis with carbon nanotube arrays." Nanotechnology 17(19): 4845-4853.

(56) References Cited

OTHER PUBLICATIONS

Creel, C.J., M.A. Lovich, and E.R. Edelman, Arterial paclitaxel distribution and deposition. Circulation Research, 2000. 86(8): p. 879-884.

Scheller, B., U. Speck, C. Abramjuk, U. Bernhardt, M. Bohm, and G. Nickenig. Paclitaxel balloon coating, a novel method for prevention and therapy of restenosis. Circulation, 2004. 110(7): p. 810-814.

Bronikowski, M.J., Longer nanotubes at lower temperatures: The influence of effective activation energies on carbon nanotube growth by thermal chemical vapor deposition. Journal of Physical Chemistry C, 2007. 111(48): p. 17705-17712.

Sinha, N., et al., "Carbon Nanotubes for Biomedical Application," IEEE Transactions on Nanobioscience, IEEE Service Center, Piscataway, NY, vol. 4, No. 2, Jun. 1, 2005, pp. 180-195.

PCT International Search Report and the Written Opinion of the International Searching Authority for PCT/US2010/000243.

Liming Dai, et al., "Functionalized surfaces based on polymers and carbon nanotubes for some biomedical and optoelectronic applications," Nanotechnology, vol. 14, No. 10, Oct. 1, 2003, pp. 1084-1097.

* cited by examiner

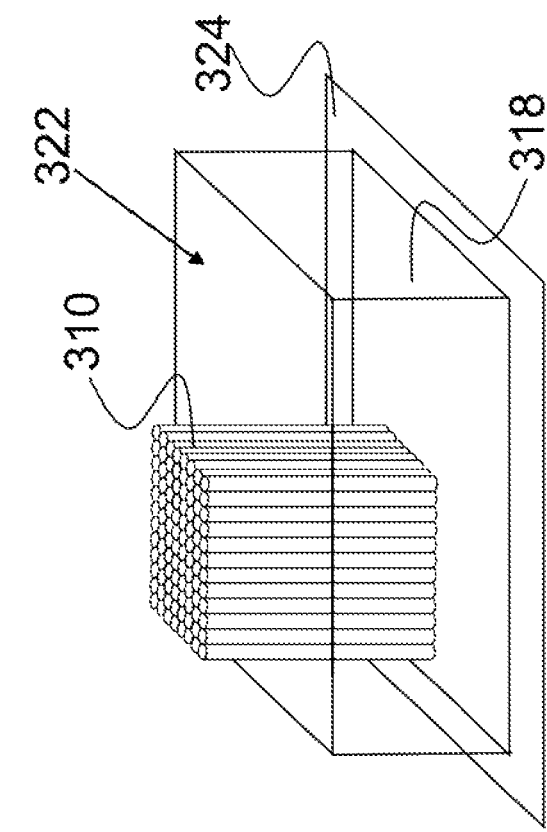
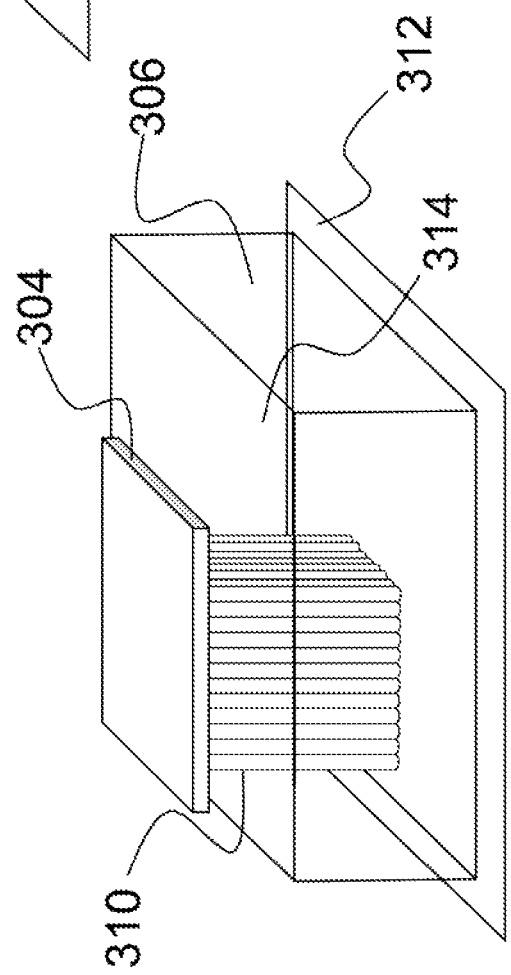
FIG. 3A
FIG. 3B
FIG. 3C

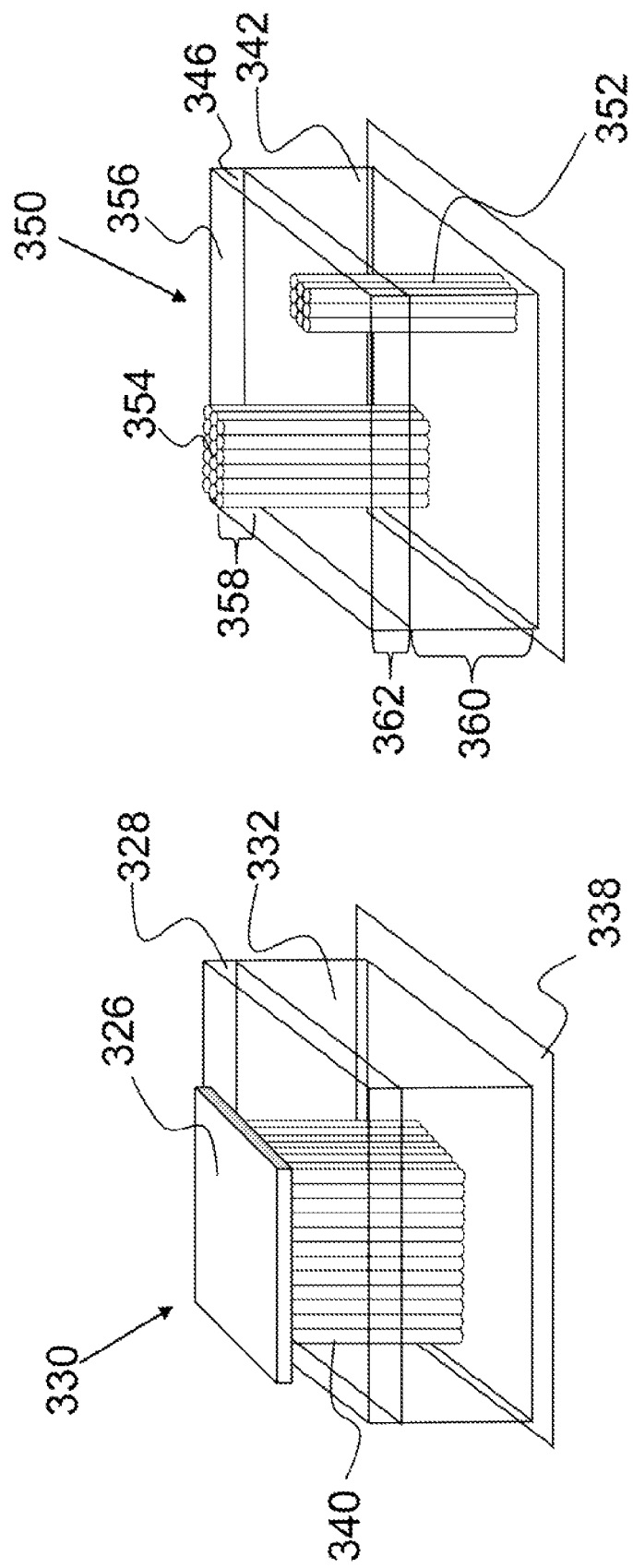

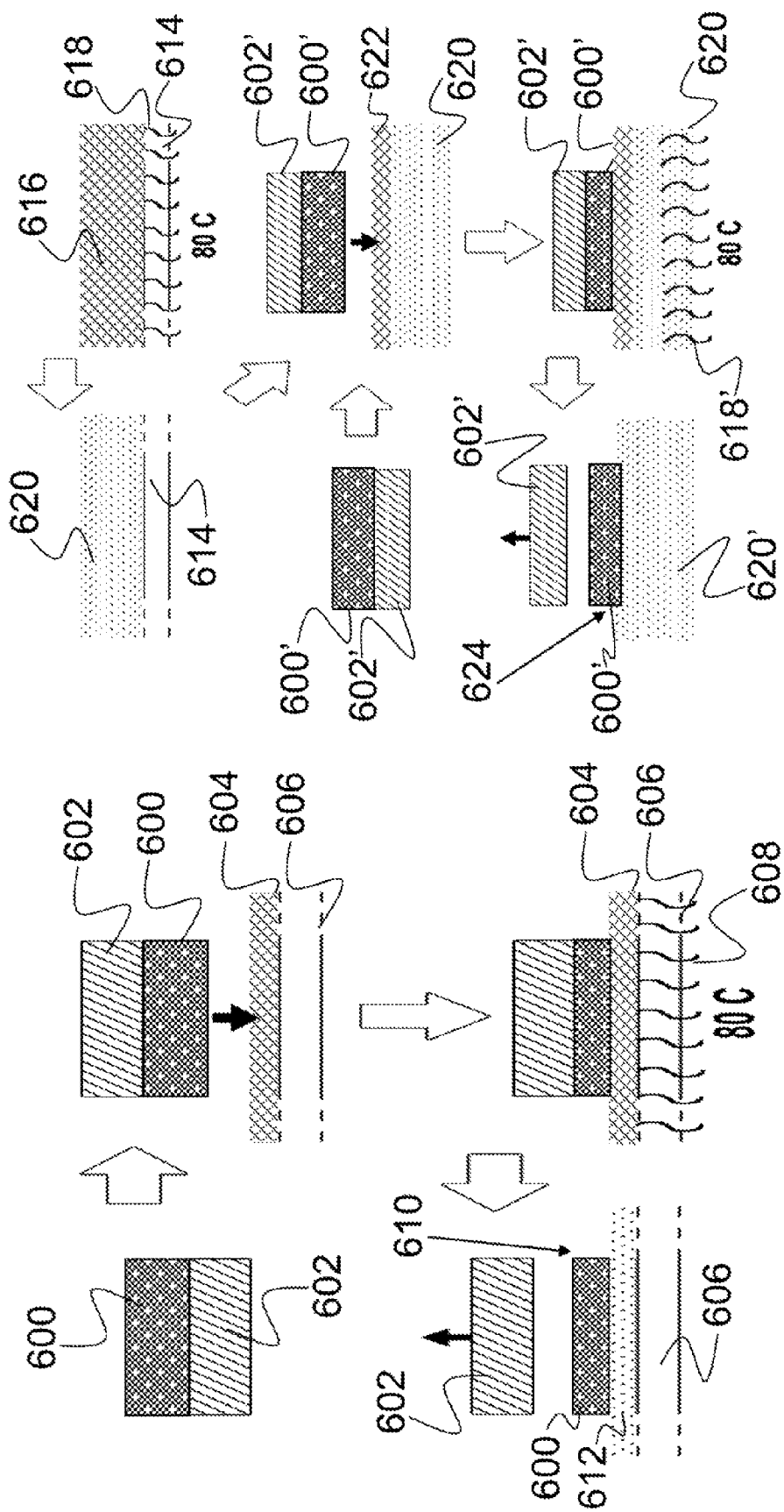

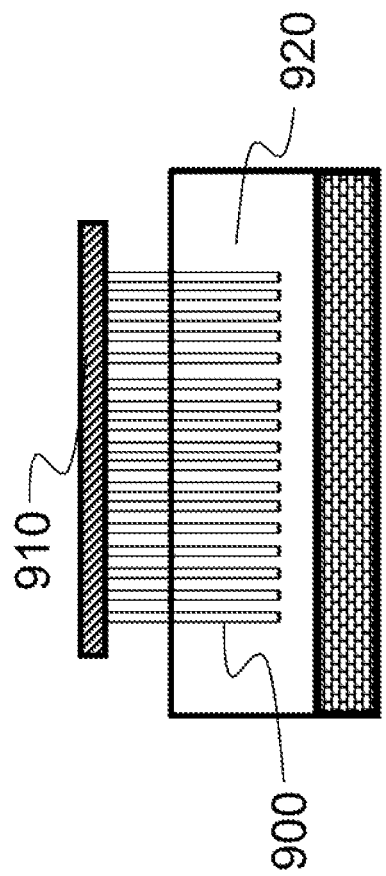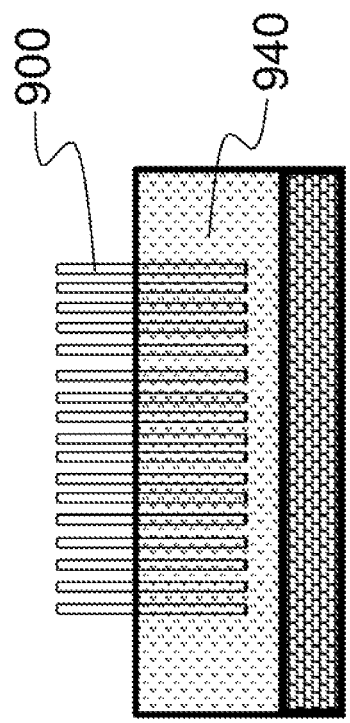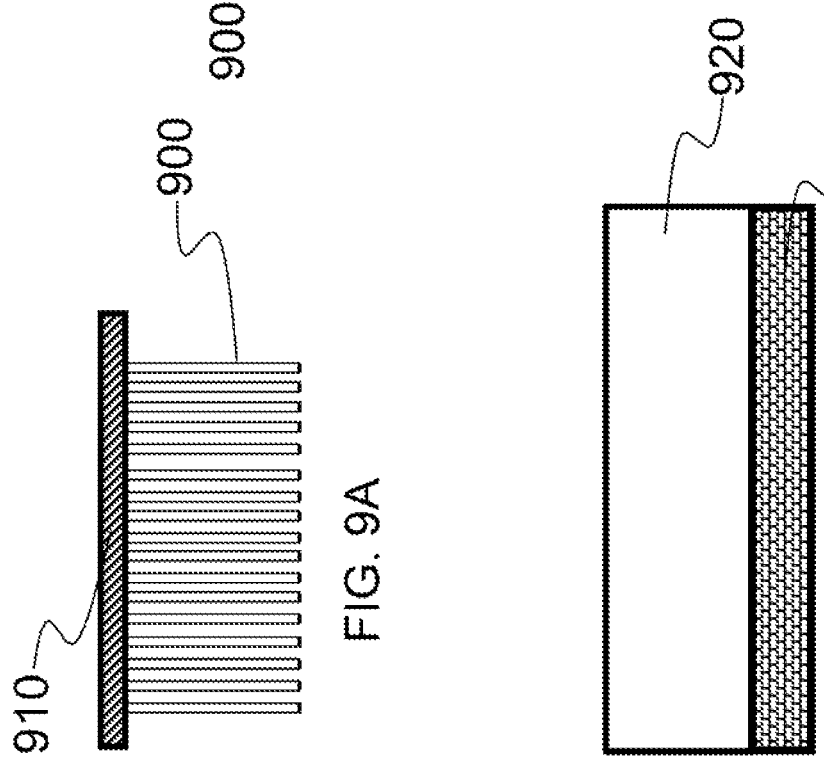

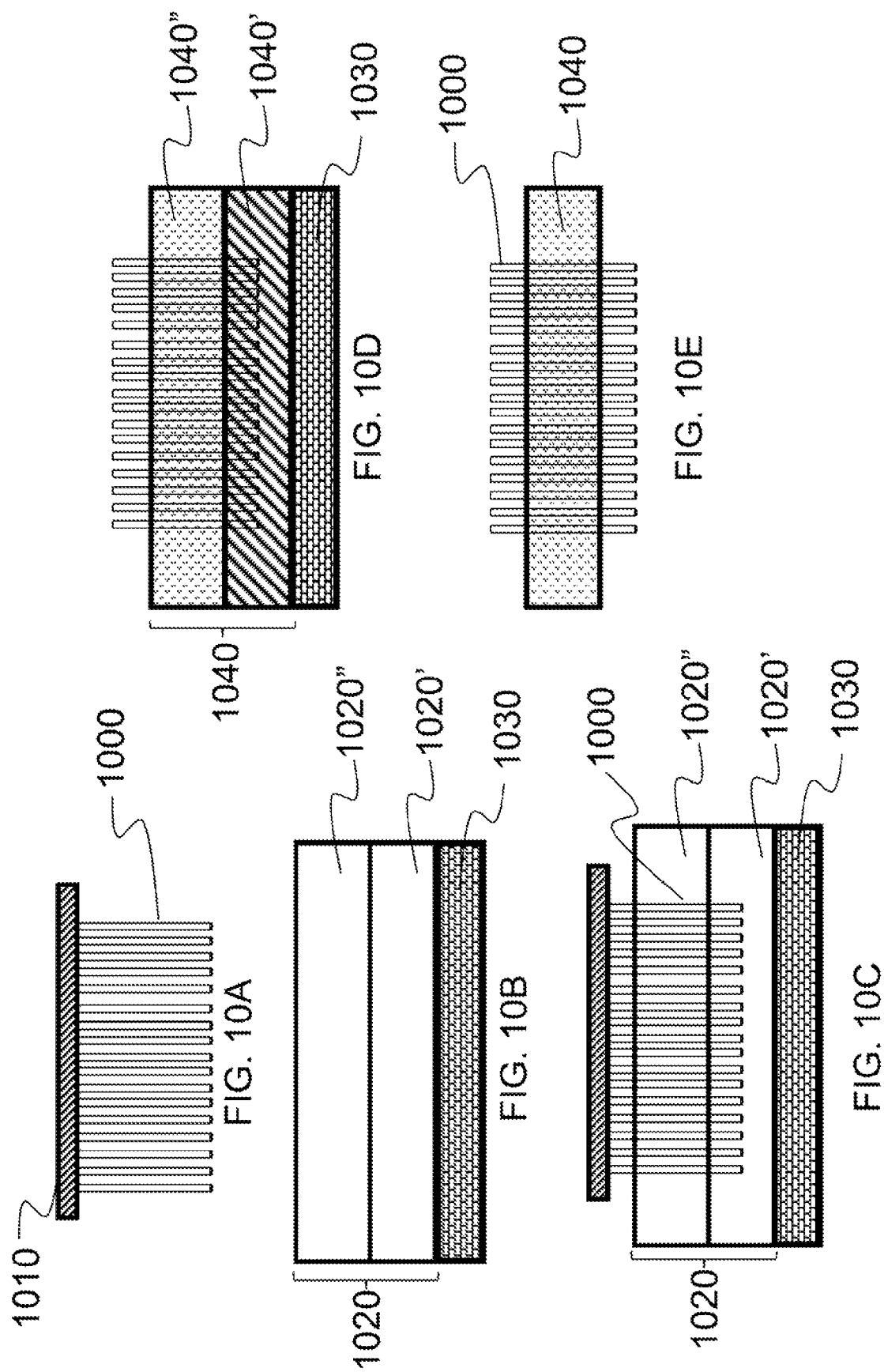

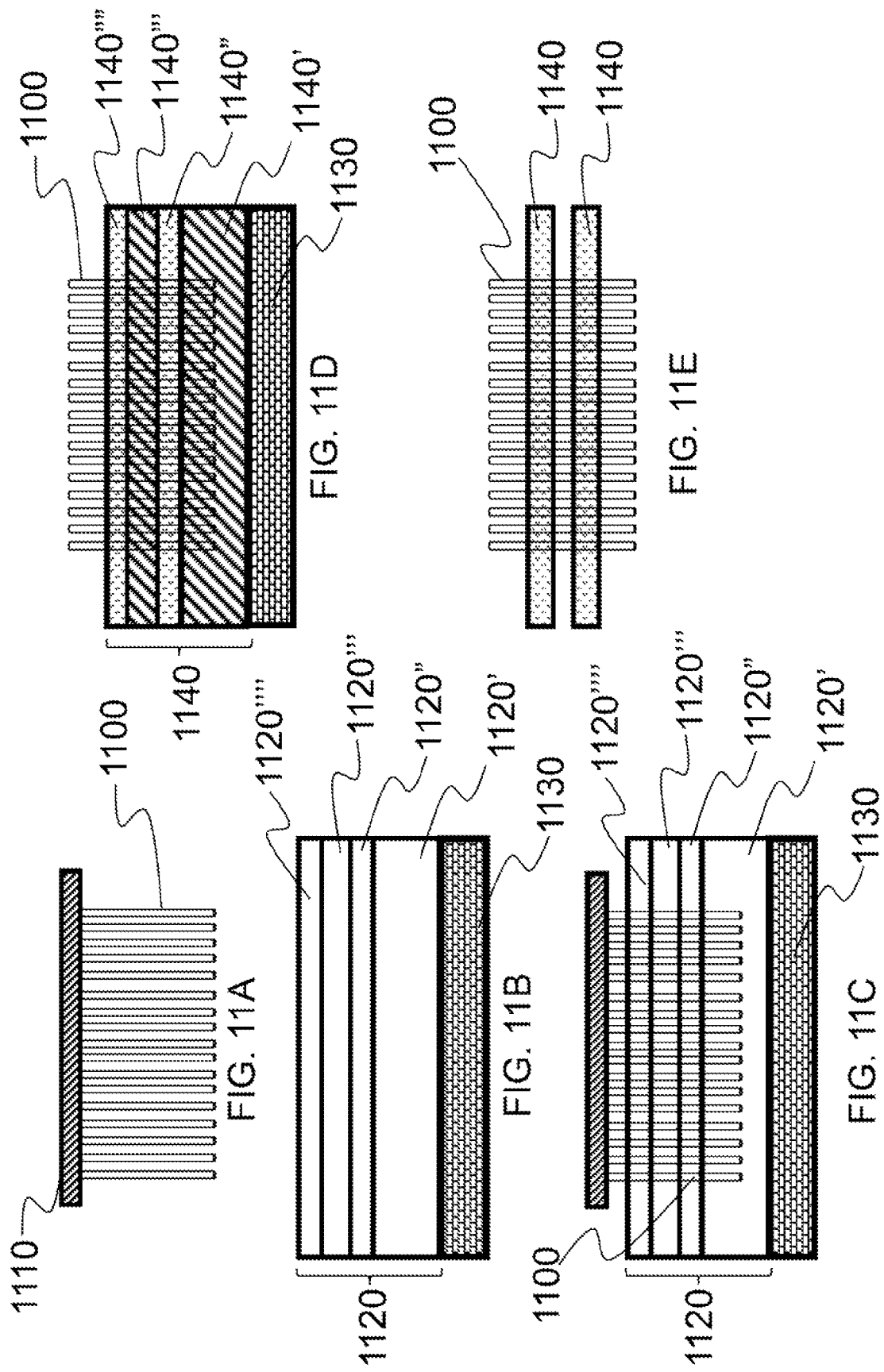

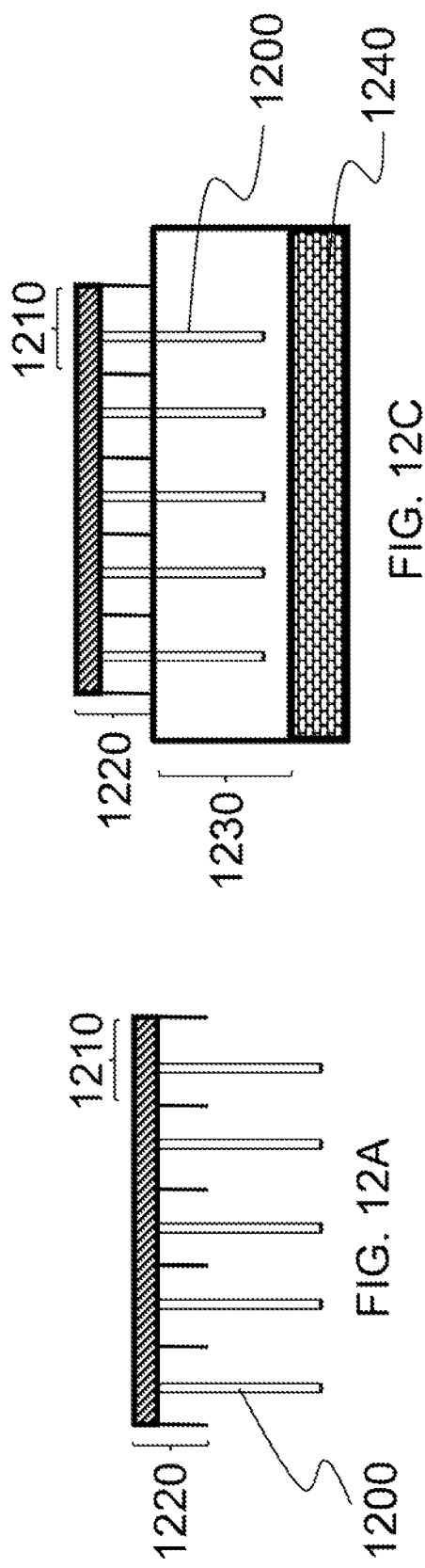
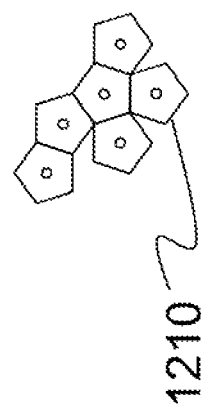
FIG. 12C
FIG. 12D
FIG. 12A
FIG. 12B

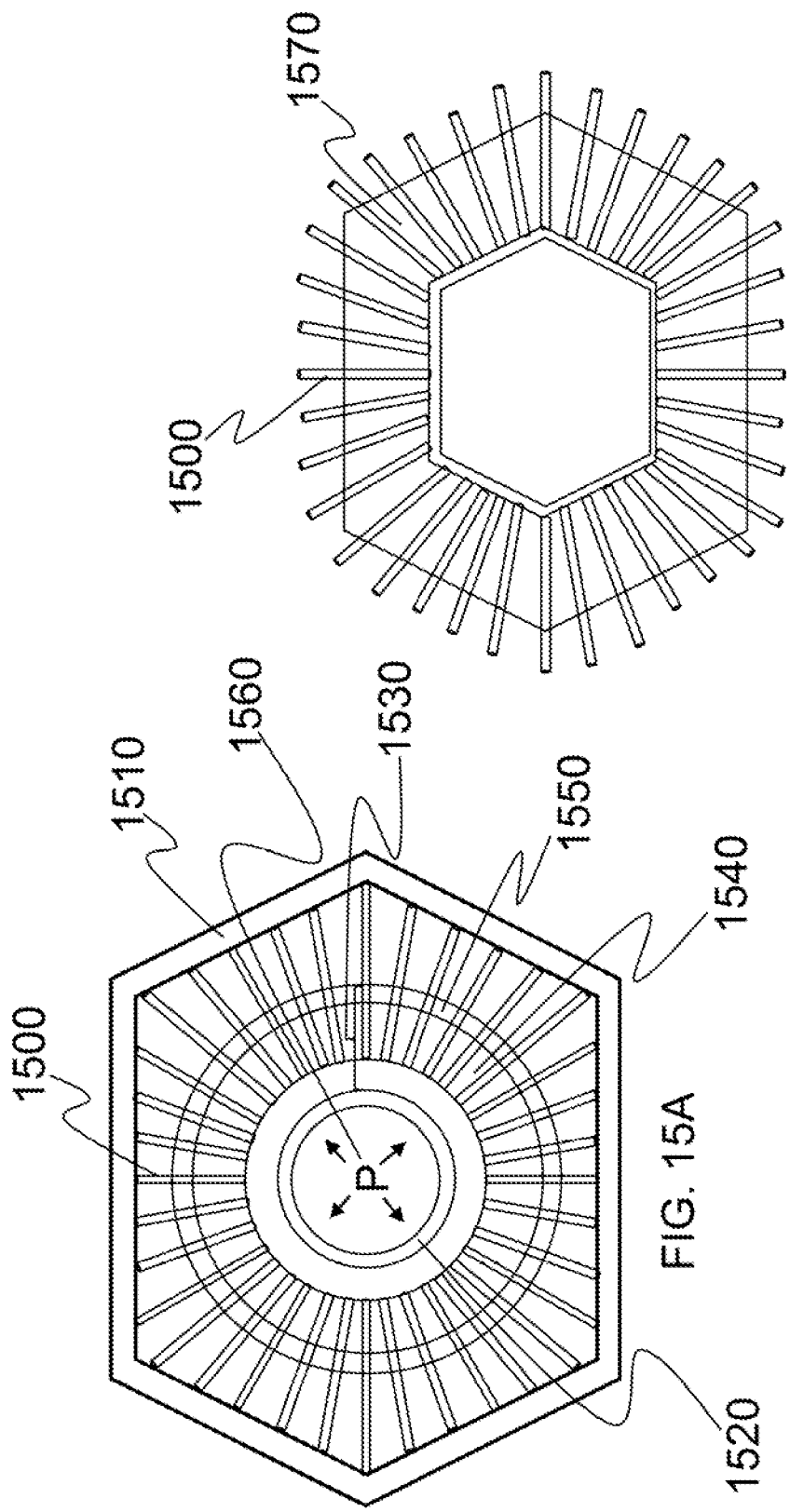

METHOD FOR SELECTIVELY ANCHORING AND EXPOSING LARGE NUMBERS OF NANOSCALE STRUCTURES

PRIORITY CLAIM

The present application is a continuation-in-part of U.S. patent application Ser. No. 11/827,169, filed Jul. 10, 2007, titled "Method for Anchoring Large Numbers of Nanoscale Structures" which, in turn, claims priority to U.S. Provisional Patent Application No. 60/819,872, filed Jul. 10, 2006, titled, "Method for Anchoring Large Numbers of Nanoscale Structures."

BACKGROUND OF THE INVENTION (1) Technical Field

The present invention is generally directed to processes for forming structures incorporating nanoscale objects and more particularly, to selective anchoring and exposure of nanoscale structures within an anchoring structure.

(2) Description of Related Art (2.1) Nanostructure Properties and Applications

Nanostructures are widely expected to bring about major technological advances. For more than a decade, nanostructures have been the subject of intense study, both in characterization and fabrication. Nanotubes are an integral component in devices requiring reduced power consumption, reduced mass, and extreme functional gains through economies of scale. Unlike larger-scale materials and devices of the same composition, the size-dependent properties of nanoscale devices greatly benefit from their small length scales.

Nanoscale devices are currently only intended for applications in highly-controlled environments. This general lack of robustness in "everyday" environments is a key factor inhibiting the realization of useful nanoscale-based devices. Potentially damaging environmental considerations which bar the use of nanostructures in an environment include the presence of: airborne particles, fluids, impacts and interactions with solid surfaces, and potential interactions with factors such as undesirable temperatures, fluid flows, and chemical reactions. Typical solutions to these environmental hazards involve performing experiments, conducting additional device development, and performing fabrication under highly controlled conditions (usually within a "clean room"). As a result, nanoscale devices are typically restricted to applications in which the devices are in an environment where potentially damaging environmental interactions can be controlled.

A wide variety of useful applications for nanostructures exist. However, lack of viable solutions which mitigate these environmental hazards posed to nano-based technologies typically prohibits them from being used in these applications. A small sample of these applications includes flat-panel displays based on field emissions and hydrodynamic drag-reducing nano- and micro-structured skins and surfaces.

(2.2) Nanostructure Composites

One solution has been to fully immerse the nanostructures within curable materials, thereby forming a composite. Such composites augment mechanical properties such as the elastic modulus and toughness of the nanostructure. In general, this is accomplished by distributing impact forces across the large surface area of the curable material, transferring the force through the composite instead of directly through the nanostructure, and out the bottom surface area of the composite.

Recent developments, specifically in the field of post-fabrication production, have focused on addressing design considerations for fields which have had long felt needs. Most post-fabrication production research has been on developing solutions to the problem of overcoming existing environmental conditions which have historically been unfavorable to nanostructures. As mentioned above, one recent development has focused on immersing nanostructures within curable materials in order to form a nanostructure composite. Composites often consist of a combination of polymeric materials and carbon nanotubes, but the techniques for producing them characteristically lack control of nanotube placement.

One such post-fabrication handling technique uses fixed nanostructures within a deposit of silicon oxide pads via a lithographic shadowmask process onto SiC nanorods and multi-walled carbon nanotubes dispersed on an atomically flat $MoS_2$ surface, leaving some of the nanostructures protruding from the edges of the pads (Wong et al. 1997).

Another method involves dispersing arc-discharge-grown carbon nanotubes within a temperature-cured epoxy resin, curing, and then thinly slicing the composite with a microtome, leaving the nanotubes well-aligned and either fully embedded or tangent to and flush with the slice surfaces (Ajayan et al. 1994).

A further method involves using a blade to smear a UV-curable epoxy over carbon nanotubes deposited onto a surface from a solution, followed by UV curing and mechanical testing (Wagner et al. 1998).

Still another method involves the dispersion of ground arc-discharge grown carbon nanotubes in a thermoplastic polymer, time curing a layer sitting on a Teflon surface, and peeling off the nanotube-polymer composite for mechanical tests (Jin et al. 1998).

Another method uses a chemical vapor deposition growth of aligned arrays of carbon nanotubes followed by submersion of the entire sample and growth substrate within a curable polymer (PMMA or PDMS) solution, followed by curing and removing of the nanotube-polymer composite (Raravikar et al. 2005).

A still further method involves Van der Waals-based attachment of a single carbon nanotube to an etched tungsten tip followed by covering the tungsten tip and the base of the carbon nanotube with a UV-curable polymer using native spreading of the polymer on the tip, then UV curing, leaving the tip "insulated" relative to the surroundings while the nanotube is exposed to the local environment (Boo et al. 2006).

The aforementioned methods for mechanically protecting the nanostructures suffer from unpredictable dispersal of the nanotubes within the materials, generally as illustrated in FIG. 1. In FIG. 1A, a top view of a composite material 100 is shown. The composite material 100 comprises a plurality of nanostructures 104 within a cured material 102. To form the composite material 102, the nanostructures 104 are placed on a layer of fluid material. Spin-coating the material prior to curing results in a largely level surface. The nanostructures 104 become randomly dispersed within the fluid material as a result of the spin-coating process. Although many nanostructures 104 are fully immersed in the cured material 102, many nanostructures 106 randomly protrude from the material 102.

In FIG. 1B, a side view of the composite material 100 is shown. Nanostructures 104 embedded within the cured layer 102 are dispersed randomly. On occasion nanostructures 106 randomly protrude from the cured layer 102. For nanostructures 104 within the cured layer 102, the cured layer 102 offers mechanical protection from impact events. However, for applications which utilize properties in addition to mechanical properties of the nanostructures 104, the nanostructures 106 protruding from surfaces do not protrude with enough regularity and specificity to take advantage of these properties. As such, there is a need for the ability to controllably disperse the nanostructures 104 within a cured layer 102 (polymer) to achieving sufficient wetting, adhesion, and mechanical load transfer between the cured layer and the nanostructures (Xie et al. 2005). There is a further need for the ability to control the depth of a nanostructure 104 within the cured layer 102.

Nanostructure composite 100 manufacturing techniques, as they exist in the art, lack the ability to control the orientation and depth of the nanostructures 104 within the cured layer 102. Therefore, applications requiring anchored partially-immersed nanostructures 106 within a cured layer, such as growth templates for cell and tissue cultures, are unable to take advantage of enhanced characteristics offered by nanostructure composites 100.

Other works have dealt with related topics. None have shown controllable anchoring of wholly immersed nanostructures 104 or partially immersed nanostructures 106 having free ends in exact configurations. For example, in the work of Lahiff et al. 2003, the authors describe that "a thin-film of polydimethylsiloxane (PDMS) was spin coated onto the nanotube film." Surprisingly the authors further disclose " . . . which indicates that it is possible only the very tips of the tubes that project from the PDMS surface." The projection of the exposed nanotube tips from the surface has not proven controllable. In general, the act of spin coating is an imprecise method with no mechanism for controllably immersing a nanostructure within a fluid, such as PDMS.

In other work, Jung et al. 2006, the authors considered the field emission results from their samples, prepared as in Lahiff et al. 2003. The authors state "Scanning Electron Microscope images (not shown) of our functional devices show that the very few tips that are exposed above the PDMS surface are 2-3 μm long and are separated by distances of similar or larger lengths." Using their approach, the few tips exposed from the surface of the PDMS could not be shown to be controllable. The authors further failed to provide any quantification of how many tips are exposed, a guarantee of reproducibility, or an ability to adjust the degree of protrusion above the surface.

The above methods unintentionally and uncontrollably result in carbon nanotubes (or, more generally, nanostructures) protruding from the upper surface of their PDMS. As a result, using methods that apply a curable polymer on top of the nanostructures offers no repeatable means of control of the number of nanostructures protruding through the surface or the extent of their protrusion. Even when combining a spin-coating procedure with the above procedure, no control over the resulting length of the protrusion of the nanostructures from the surface of the PDMS is demonstrated. Further, residual polymer is likely to cover all portions of the surface since PDMS has been shown to be highly wetting on carbon nanotubes Barber et al. 2004 (PDMS also easily wets many other materials).

Additionally, spin-coating of a material using a highly viscous fluid, such as curable PDMS, on top of nanostructures will significantly alter the nanostructures' local relative configurations. This unavoidable drawback would prevent the formation of specific (pre-determined) small-scale patterns of nanostructures within the cured material.

The above methods fail to provide for control of the overall pattern of nanostructures embedded within the cured layer. A need also exists for controlling the depth and overall height of a nanostructure protruding from a surface. A further need exists for preserving a preexisting pattern of nanostructures within, and optionally exposed or protruding from, the cured layer. A still further need exists for a method that provides a mass-produced composite formed with repeating patterns of nanostructures. A still further need exists for a method that provides the ability to selectively embed specific nanostructures from a group of nanostructures into a composite.

SUMMARY OF THE INVENTION

The present invention overcomes the aforementioned shortcomings in the prior art. The present invention teaches a method for fastening a plurality of nanoscale structures within an anchoring structure to form a nanostructure composite and nanostructure composites formed therefrom.

In one aspect, the method of the present invention teaches providing a primary fluid layer on an anchoring substrate. Also, a plurality of nanostructures is provided on an initial substrate selected from a group consisting of a growth substrate on which the nanostructures were grown and an anchoring structure, the nanostructures each having a defined height and orientation with respect to the initial substrate. The plurality of nanostructures is introduced to a desired depth in the primary fluid layer, such that the orientation of the nanostructures relative to the growth substrate is substantially maintained; where the primary fluid layer comprises multiple fluid layers. Ones of the multiple fluid layers are selected such that when altered to form an anchoring structure, a portion of the anchoring structure can be removed, leaving an anchoring structure permitting exposure of at least a portion of the nanostructures.

In another aspect, the present invention teaches that the fluid layers are selected such that when altered to form an anchoring structure a portion of the anchoring structure can be removed permitting the exposure of at least a number of nanostructures through two sides of the anchoring structure.

In a further aspect, the invention further comprises altering the fluid layers to form an anchoring structure, thereby affixing at least a portion of the nanostructures within the anchoring structure, whereby when the initial substrate is a growth substrate, the growth substrate may be removed, leaving at least a portion of the nanostructures affixed within the anchoring structure.

In a still further aspect, the invention further comprises removing a portion of the anchoring structure, permitting exposure of at least a number of nanostructures through two sides of the anchoring structure.

In a yet further aspect, when the initial substrate is a growth substrate, the present invention teaches removing the growth substrate to leave a set of nanostructures, where at least a portion of the nanostructures is affixed within the anchoring structure.

In another aspect, the growth substrate comprises a set of nanostructure cells, the nanostructures each having a defined height and orientation with respect to the growth substrate, where the nanostructures extend beyond the nanostructure cells. In the act of introducing the plurality of nanostructures to a desired depth in the primary fluid layer, the nanostructure cells are made to contact the primary fluid layer. As a result, nanostructures extend beyond the primary fluid layer by a depth approximately equal to a depth of the nanostructure cells.

In a further aspect, the depth of the nanostructure cells is selected prior to growth of the nanostructures, thereby providing varying lengths of nanostructures beyond the fluid layer.

In a yet further aspect, ones of the multiple fluid layers are stratified with respect to other ones of the multiple fluid layers, such that ones of the multiple fluid layers may be altered independently of others of the multiple fluid layers to form the anchoring structure. As a result, the growth substrate and at least a portion of the anchoring structure may be removed to permit exposure of at least a portion of the nanostructures.

In a still further aspect, the multiple fluid layers are stratified with respect to each other by a property selected from the group of pressure, density, viscosity, immiscibility, and phobicity, and where materials for the fluid layers are selected to permit selective altering of various ones of the fluid layers to allow selected portions of the nanostructures to be anchored in various portions of the anchoring structure.

In another aspect, the products fabricated by the methods of the present invention are taught.

In a further aspect, the present invention teaches a method for fastening a plurality of nanoscale structures within an anchoring structure, including an act of providing a primary fluid layer on an anchoring substrate. Also, a plurality of nanostructures is provided on a growth substrate on which the nanostructures were grown, the nanostructures each having a defined height and orientation with respect to the growth substrate. Next, the plurality of nanostructures is introduced to a desired depth in the primary fluid layer, such that the orientation of the nanostructures relative to the growth substrate is substantially maintained. In this aspect, the primary fluid layer comprises multiple fluid layers. The fluid layers are selected such that when altered to form an anchoring structure a portion of the anchoring structure can be removed, permitting exposure of the nanostructures through two sides of a remainder anchoring structure.

In yet another aspect, the primary fluid layer is altered to form an anchoring structure, thereby affixing at least a portion of the nanostructures within the anchoring structure, whereby the growth substrate may be removed, leaving at least a portion of the nanostructures affixed within the anchoring structure.

In a still further aspect, the growth substrate is removed to leave a set of nanostructures, where at least a portion of the nanostructures is affixed within the anchoring structure.

In a further aspect, the nanostructures are carbon nanotubes.

In another aspect, the nanostructures are arranged in a pattern on the growth substrate.

In yet another aspect, the act of providing the anchoring structure on the anchoring substrate is accomplished by spin-coating at least a portion of the fluid layer onto the anchoring substrate to provide a substantially uniform thickness.

In another aspect, the plurality of nanostructures is comprised of different materials.

In a further aspect, products fabricated by the methods of the present invention are taught.

In a still further aspect, the present invention teaches a plurality of nanoscale structures fastened within an anchoring structure, including a plurality of nanostructures each having a defined height and orientation and an anchoring structure, formed such that at least a portion of the nanostructure is exposed from the anchoring structure.

In a still further aspect, the portion of the nanostructure exposed from the anchoring structure is at least one end of the nanostructures.

BRIEF DESCRIPTION OF THE DRAWINGS

The objects, features and advantages of the present invention will be apparent from the following detailed descriptions of the disclosed aspects of the invention in conjunction with reference to the following drawings, where:

FIG. 3A is a top view of an illustration of a plurality of nanostructures attached with and supported by a surface;

FIG. 3B is an illustration of a plurality of nanostructures attached with a surface at one end of the structure and partially immersed by a primary fluid layer at the other;

FIG. 3C is an illustration of a plurality of nanostructures partially immersed within a composite;

FIG. 3D is an illustration of a plurality of nanostructures partially immersed within a composite formed of first anchoring structure and second primary fluid layer;

FIG. 3E is an illustration of two groups of nanostructures, each having a particular configuration, with each group of nanostructures being partially surrounded within a composite formed of first anchoring and second anchoring structures;

FIG. 6A is schematic representation of the formation of a single anchoring structure carbon nanotube composite;

FIG. 6B is schematic representation of the formation of a carbon nanotube composite having two similar anchoring structures;

FIG. 9A is a side view illustration showing a plurality of nanostructures grown on a growth substrate;

FIG. 9B is a side view illustration of a primary fluid layer on an anchoring substrate;

FIG. 9C is a side view illustration showing a plurality of nanostructures attached with a growth substrate at one end of the structure and partially embedded within a primary fluid layer at the other;

FIG. 9D is a side view illustration showing a plurality of nanostructures partially embedded within an anchoring structure;

FIG. 10A is a side view illustration showing a plurality of nanostructures grown on a growth substrate;

FIG. 10B is a side view illustration of a primary fluid layer on an anchoring substrate, where the primary fluid layer comprises of two fluid layers;

FIG. 10C is a side view illustration showing a plurality of nanostructures attached with a growth substrate at one end of the structure and partially embedded within a primary fluid layer at the other, where the primary fluid layer comprises of two fluid layers;

FIG. 10D is a side view illustration showing a plurality of nanostructures partially embedded within an anchoring structure;

FIG. 10E is a side view illustration showing a plurality of nanostructures partially embedded within an anchoring structure after removal of the anchoring substrate and one of the fluid layers;

FIG. 11A is a side view illustration showing a plurality of nanostructures grown on a growth substrate;

FIG. 11B is a side view illustration of a primary fluid layer on an anchoring substrate, where the primary fluid layer comprises of multiple fluid layers;

FIG. 11C is a side view illustration showing a plurality of nanostructures attached with a growth substrate at one end of the structure and partially embedded within a primary fluid layer at the other, where the primary fluid layer comprises of multiple fluid layers;

FIG. 11D is a side view illustration showing a plurality of nanostructures partially embedded within an anchoring structure;

FIG. 11E is a side view illustration showing a plurality of nanostructures partially embedded within an anchoring structure after removal of the anchoring substrate and ones of the fluid layers;

FIG. 12A is a side view illustration showing a plurality of nanostructures grown on a growth substrate, where the nanostructures are grown in nanostructure cells;

FIG. 12B is a side view illustration showing a plurality of nanostructures grown on a growth substrate, where the nanostructures are grown in nanostructure cells and the nanostructure cells have varying heights/depths;

FIG. 12C is a side view illustration showing a plurality of nanostructures immersed in a primary fluid layer on an anchoring substrate to a depth where the nanostructure cells contact the fluid layer;

FIG. 12D is a top view illustration showing a plurality of nanostructures inside nanostructure cells;

FIG. 15A is a side view illustration showing a plurality of nanostructures grown on a hexagonal growth substrate;

FIG. 15B is a side view illustration showing a plurality of nanostructures partially embedded within an anchoring structure, where the final anchoring structure is hexagonal;

DETAILED DESCRIPTION

Figure 1:
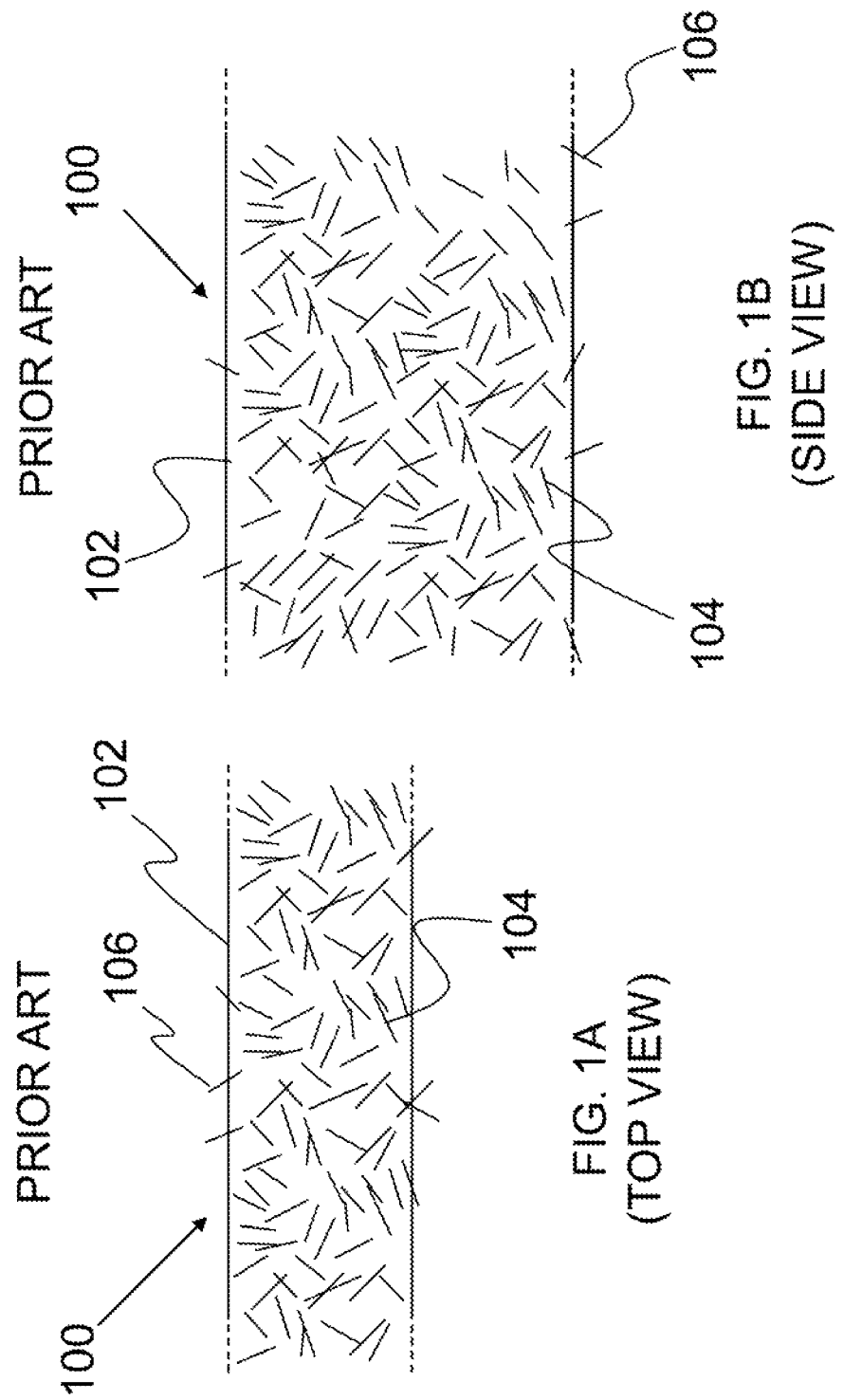
FIG. 1A is a top view illustration showing a composition consisting of a plurality of nanostructures randomly dispersed.
FIG. 1B is a side view illustration showing a composition consisting of a plurality of nanostructures randomly dispersed.

The present invention relates to a method for creating nanostructure composites by combining and controlling the placement of pre-fabricated nanoscale structures (nanostructures) and a variety of materials in which the nanostructures are anchored. In one aspect, the present invention teaches a nanostructure composite product comprising a plurality of nanostructures either partially or wholly immersed within an anchoring material. A variety of techniques have been contemplated that allow a plurality of nanostructures to be controllably surrounded and immersed to a specified depth and configuration within an anchoring material.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention. Note that in certain ones of the figures, the nanostructures are intentionally illustrated as being spaced far apart to more clearly show the inventive concept, where in actuality they are generally densely packed. Also as should be apparent to one of skill in the art, these figures are illustrative only and are not to scale.

The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings), may be replaced by alternative features serving the same, equivalent, or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Below, an introduction to the present invention is provided to give an understanding of the specific aspects. Then, an overview of the principal aspects of the present invention is presented. Finally, a conclusion is provided to briefly summarize the method according to the present invention.

(1) INTRODUCTION

The present invention is intended to increase mechanical strength of, enhance temperature-resistant properties of, and provide a substrate for securing nanostructures for a wide variety of applications. The nanostructures are either partially or wholly embedded within a primary fluid layer. Once the nanostructures are immersed to a desired depth within the primary fluid layer, the primary fluid layer is altered such that the nanostructures become anchored within the altered anchoring structure. The primary fluid layer may comprise multiple fluid layers, where ones of the fluid layers can be selectively altered to form the anchoring structure. The fluid layers may be selected so that only certain layers are altered. Alternately, the fluid layers may be selected such that once altered, at least one of the layers can be removed. Thus, a device is formed comprising an anchoring structure with a plurality of nanostructures embedded therein, where a portion of the nanostructures is exposed from the anchoring structure. The exposed portion of the nanostructure may include at least one end of the nanostructures or another portion of the nanostructures.

The present invention is directed to a product comprising a curable fluid and a plurality of nanostructures controllably anchored within the curable fluid. The present invention is further directed to a method for making the same.

The present invention is intended to fulfill the demand for a wide variety of applications which may have previously benefited from the integration of nanostructures within the devices, but were previously impossible due to the limitations of the nanostructure composites.

The method and apparatus of the present invention may be practiced using a wide variety of materials and configurations as should be appreciated by one of ordinary skill in the art.

A nanostructure may be formed having a variety of lengths, widths, and may also be combined with a number of other nanostructures to form a variety of configurations and patterns. The configurations may either be prefabricated by growing the nanotubes in a particular pattern, or may arise by selectively screening densely packed nanostructures. Suitable types of nanostructures include, but are not limited to nanowires, nanotubes, and nanoparticles. Nanostructures discussed below have been formed using densely-packed aligned arrays of prefabricated nanotubes.

In general, nanostructures may be formed or grown using a variety of materials. Examples of suitable materials include but are not limited to Al, In, Sn, Te, and Se. In general, any element or compound having enhanced properties on the nanoscale may be grouped together to be used to form a plurality of nanostructures. It should be appreciated that the material composition from nanostructure to nanostructure may either be homogenous or heterogeneous within a grouping of nanostructures in order to suit a wide variety of applications.

A wide variety of fluid layer materials may be used within the spirit of the present invention. Similarly, the fluid layer composition may either be homogeneous or heterogeneous. A homogeneous layer may, for example, be comprised of a single component light-cured and/or heat-cured adhesive composed primarily of polyurethane methacrylate resin while a heterogeneous layer may include a polymer plus a cross-linker. Such a structure may comprise a heat- or time-cure silicone rubber composed primarily of polydimethylsiloxane and a platinum-containing catalyst involved in the crosslinking reaction.

Suitable fluid layers should have an appropriate viscosity to accomplish the degree of coverage required for the particular application. Often, the first fluid layer is distinguished from the altered anchoring layer (anchoring structure) by its relatively high viscosity in comparison with the anchoring state. In general, the fluid layer viscosity is selected to ensure an appropriate amount of coverage amongst the individual nanostructures. A less viscous material may be selected for coating nanostructures on the periphery of the nanostructure configuration. A more viscous material may be used to sufficiently infiltrate, and disperse amongst, the nanostructures within the nanostructure configuration. The main characteristic of the anchoring structure is its suitability for anchoring the nanostructures within it.

Environmental conditions also play a roll in selecting an appropriate material for applications requiring resistance to extreme temperatures and broad temperature ranges, exposure to harsh chemicals, immersion in fluids, and exposure to UV rays. The material may also be selected to shield the nanostructures from noise in a wide variety of applications.

In order to alter the state of the fluid layer to that of an anchoring structure, a variety of techniques may be used. These techniques include but are not limited to temperature variation, light curing, and chemical altering of the fluid layer. These techniques may either permanently or reversibly alter the state of the fluid layer to an anchoring structure. An example of a reversible state change may involve a temperature decrease. The decrease in temperature may be used to induce the fluid layer to harden, thereby anchoring the nanostructures within the layer. However upon returning the fluid layer to substantially the original temperature, the anchoring material returns to its original state. In cases where the primary fluid layer comprises multiple fluid layers, a combination of these techniques may be used.

Figure 2:
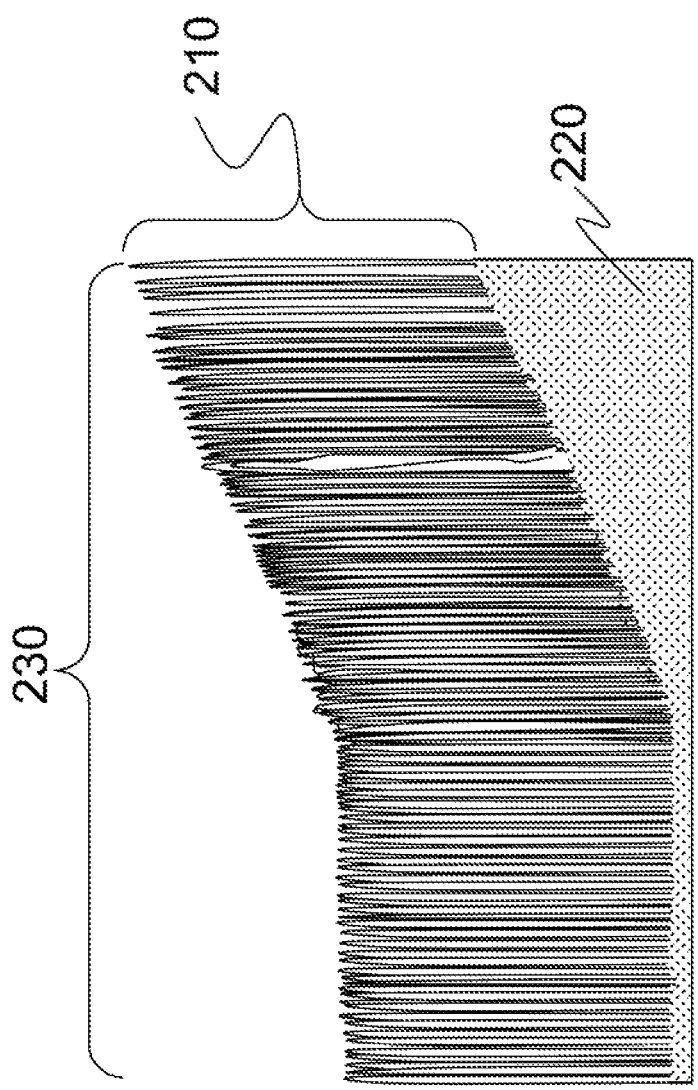
FIG. 2 is an illustration of a plurality of prefabricated carbon nanotubes on their original substrate.

Referring to FIG. 2, a cross-sectional illustration shows a plurality of nanostructures 210 residing on their fabrication substrate 220. The plurality of nanostructures 210 are densely packed carbon nanotubes 230 that have been grown in a "nanocarpet" type configuration. The nanostructures 210 are shown subsequent to fabrication by self-assembly in a thermal chemical vapor deposition (CVD).

(2) SPECIFIC DETAILS OF THE INVENTION

This invention fulfills the need for a method of anchoring nanostructures which have been formed separately, possibly in specific patterns, on another material (a growth substrate), while retaining local configurations of the nanostructures and resulting in free ends of controllable length protruding from the anchoring material, as well as exposure of other portions of the nanostructures. Use of this method allows for transfer of nanostructures from their fabrication (growth) substrates either to other substrates or to create free-standing materials, while preserving their basic physical properties and functions.

The present method of producing nanostructure composites makes possible a transfer of nanostructures from one substrate to another. In turn, substrate transfers make possible the use of nanostructures in environments in which they could not be previously used because of the substrates on which they were grown.

In FIG. 3A a plurality of nanostructures 300 in a rectangular configuration 302 is shown. The pre-fabricated nanostructures 300 are shown residing on the growth substrate 304 on which they were grown. As shown in FIG. 3B, the first act in the current method, not including the fabrication of the nanostructures 310 themselves, is the creation of a primary fluid layer 306 into which the nanostructures 310 are to be inserted. As will be described further below, the primary fluid layer 306 may comprise one fluid layer or a plurality of different fluid layers having the same or different curing or other properties. Once the known-thickness of the material (polymer) comprising the primary fluid layer 306 has been created, the plurality of nanostructures 310 is inserted into it by using their original substrate 304 for handling purposes. This step is carefully executed, without excessive compaction forces being applied to the substrate 304 in order to prevent damage being inflicted upon the nanostructures 310. Even though the length scales relevant to the nanostructures 310 are very small, the material selected for the primary fluid layer 306 has sufficient fluidity and appropriate wetting properties to easily fill the spaces between and around the nanostructures 310. When the nanostructures 310 are fully inserted, this will naturally result in the thickness of the layer of curable polymer 318 (see FIG. 3C) being equal to the depth of insertion of the nanostructures 310. Additionally, controlled positioning of the nanostructures 310 within the primary fluid layer 306 via their original substrate 304 may be performed in order to insert the nanostructures 310 to some lesser depth than the thickness of the primary fluid layer 306.

Following the insertion of the nanostructures into the primary fluid layer 306 of curable material, the primary fluid layer 306 must generally be cured by some treatment process, though it is possible to use materials which require only the passage of sufficient time in order to cure. Another example of a suitable altering (or curing) method includes heating/cooling. Altering the temperature is one useful mechanism by which the altering of the primary fluid layer 306 to an anchoring structure 318 may be expedited. The application of specific light treatments, such as applying ultraviolet lighting of sufficient intensity, and the addition of separate chemical agents to act as activators may also be used to alter the primary fluid layer 306.

The entire assembly of the primary fluid layer 306 on a substrate 312 along with the nanostructures 310 attached to the growth substrate 304 and immersed in the fluid layer, is subjected to the curing or altering process to form the anchoring structure 318 shown in FIG. 3C. Once the altering process has been completed, the nanostructures 310 are anchored in the anchoring structure 318.

In general, nanostructures 300 are not inherently well-attached to their growth substrates 304 without additional treatments. Following the transformation of the primary fluid layer 306 into the anchoring structure 318, the nanostructures 310 are firmly anchored, and the original growth substrate 304 of the nanostructures 310 may now be easily removed. Removing the growth substrate 304 from the nanostructure 310 is carefully carried out depending on the necessity for preservation of the original patterns 302 and local configurations of the nanostructures 300. By lifting off the original growth substrate 304, the nanostructures 310 are left anchored within the anchoring structure 318, whereby the depth of their anchoring is controlled by the earlier acts in the method. The "base" of the nanostructures (the ends that were adjacent to their original substrate) now becomes their "top" (the ends that are furthest from the surface of the anchoring structure 318). The nanostructures 310 are thus inverted by application of the present method. Of course, in embodiments where two ends of the nanostructures 310 are exposed beyond the anchoring structure 318, this "inversion" would not necessarily be apparent in the final device.

Referring back to FIG. 3B, the nanostructures 310 may be surrounded by the primary fluid layer 306 a number of ways. One such way is to physically immerse the nanostructures 310 into the primary fluid layer 306 by lowering the nanostructures 310 into the primary fluid layer 306 in a controlled manner. Another alternative process involves suspending the nanostructures 310 by a support surface 304 over a substrate 312, and pouring the primary fluid layer 306 onto the substrate 312. The support surface 304 is generally the substrate on which the nanostructures 310 were originally grown. The primary fluid layer 306 is poured up to a predetermined height such that the nanostructures 310 are partially or wholly immersed in the primary fluid layer 306. The primary fluid layer 306 may then be allowed to settle, forming a substantially uniform surface 314. In the case of multiple fluid layers, stratification of the layers occurs during settling. Similarly an unaltered primary fluid layer 306 may be spread to a specified thickness on the rigid, solid substrate 312 and allowed to settle at a substantially uniform height. An alternative microfabrication process of using highly repeatable centrifugal forces to spread fluid layers 306 to a desired thickness, called spin-coating, is well-known.

Altering the primary fluid layer 306 and removing the original support surface 304 on which nanostructures 310 may either rest or be attached, as shown in FIG. 3B, yields the nanostructure composite 322 shown in FIG. 3C.

Referring again to FIG. 3C, a plurality of nanostructures 310 is shown anchored within the anchoring structure 318. The properties of the anchoring structure 318 may be modified in order to suit a variety of applications. The nature of the anchoring structure 318 normally depends upon the original material used for the primary fluid layer 306 (see FIG. 3B) and the method by which the primary fluid layer 306 is altered. Chemically altering the primary fluid layer 306 is one such method that may be used to give rise to anchoring structure 318 which exhibits dramatically different properties from those that might have otherwise have been expected given the characteristics of the original primary fluid layer 306. Again, although the alteration of the primary fluid layer 306 is generally discussed herein as being through chemical means, forming the altered anchoring structure 318 may be accomplished a number of ways as will be appreciated by one having ordinary skill in the art.

In FIG. 3D a first anchoring structure 332 residing on a substrate 338 is shown covered by an uncured second primary fluid layer 328 of either the same or different material having a specified thickness. The thickness of the first anchoring structure 332 and second primary fluid layer 328 may be modified to suit the environment for which the nanostructure composite 330 is intended. Although shown with the supporting surface 326, the supporting surface 326 may be removed prior to surrounding the nanostructures 340 with the second primary fluid layer 328. The first anchoring structure 332 may be covered by any number of primary fluid layers 328. Each primary fluid layer 328 may be selected to enhance the overall suitability of the nanostructure composite 330 and subsequently altered to fulfill its intended use. With respect to the plurality of primary fluid layers 328 and 332, the nanostructure composite 330 may be formed of either a homogenous or heterogeneous composition.

In FIG. 3E a nanostructure composite 350 comprising a first nanostructure configuration 352 and second nanostructure configuration 354 at varying depths within a first anchoring structure 342 and second anchoring structure 346 is shown. Although the first nanostructure configuration 352 and second nanostructure configuration 354 are shown as substantially rectangular in shape, a variety of other shapes are also possible. The first nanostructure configuration 352 and second nanostructure configuration 354 are separated by a controlled distance. This distance may be achieved by surrounding a first plurality of nanostructure configurations 302, as shown in FIG. 3A, into a first fluid material, followed by surrounding a separate but similar second nanostructure configuration 302 at the specified distance. Alternatively the first nanostructure configuration 352 and second nanostructure configuration 354 may be selectively grown with a desired distance of separation. In a further alternative the first nanostructure configuration 352 and second nanostructure configuration 354 may be grown from a dense carpet of nanostructures 300 as shown in FIG. 3A. By carefully removing nanostructures residing on the growth substrate 304, the first nanostructure configuration 352 and second nanostructure configuration 354 may be formed. Masking may be employed so that the first primary fluid layer 332 and the second primary fluid layer 328 cover different surface areas.

The depth of insertion, or the depth of the first nanostructure configuration 352 and second nanostructure configuration 354 within a first anchoring structure 342 and second anchoring structure 346 may be controlled in order to establish a desired height of protrusion 358 from the surface 356 of the second anchoring structure 346. Alternatively the length of protrusion 358 may be controlled by increasing or decreasing the height 360 of the first anchoring structure 342 and of the height 362 of the second anchoring structure 346.

The first anchoring structure 342 may be selected such that it will adhere strongly to a second anchoring structure 346 comprised of a different composition. Adhesion between a first anchoring structure 342 and a second anchoring structure 346 may also be accomplished by adding an epoxy or other suitable material subsequent to forming the first anchoring structure 342 but prior to forming the second anchoring structure 346. Alternatively if the first anchoring structure 342 and second anchoring structure 346 are homogeneous, then the nanostructure composite 350 will typically function as though the composite 350 was composed of one single continuous structure rather than being composed of two or more separately created structure 342 and 346. This feature is foreseen to be extremely useful in applications of anchored nanostructures 352 and 354 which require sufficiently thick structures (layers) 342 and 346 so as to be mechanically resilient and easy to manipulate, but where thin films of 50 µm, for example, would be much too weak for use. Typically nanostructures on a substrate are considered to have at most one dimension of 100 µm or so, but not typically greater. Therefore structures 342 and 346 of an aggregate thickness equal to the anchoring depth consisting of the height 360 of the first anchoring structure 342 and of the height 362 of the second anchoring structure 346, will be quite thin.

Figure 4B:
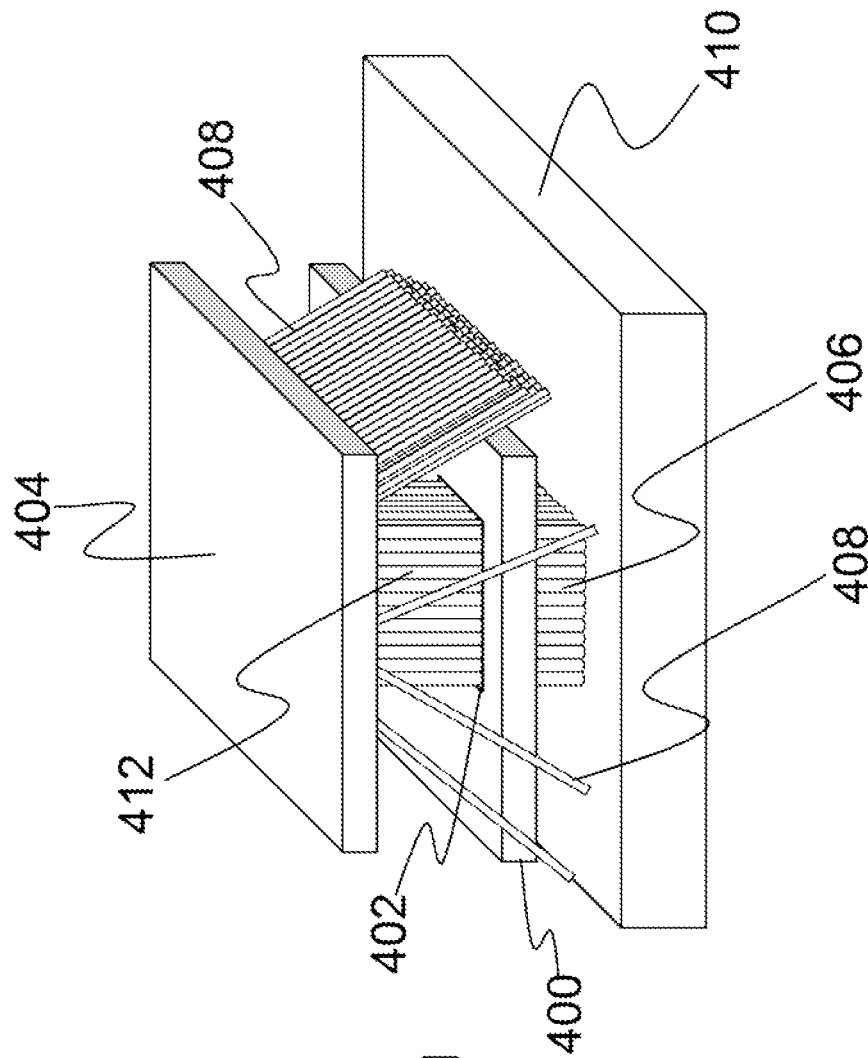
FIG. 4B is an illustration of a plurality of nanostructures supported by a surface and superimposed on a mask for selectively embedding the plurality of nanostructures within the composite.
Figure 4A:
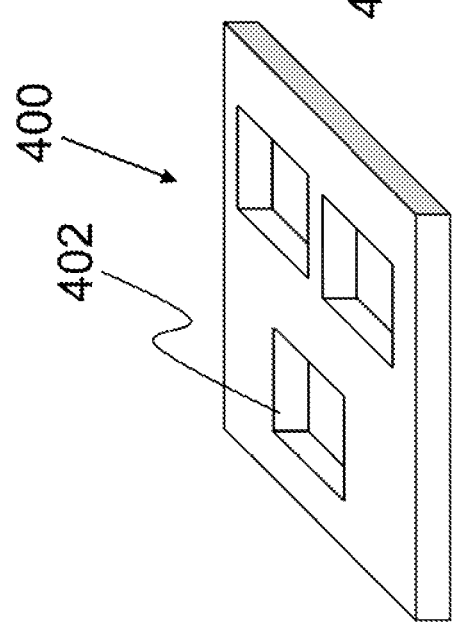
FIG. 4A is an illustration of a nanostructure mask for selectively generating a desired nanostructure configuration.

In FIG. 4A a mask 400 is shown which has an overall height which is less than the length of the nanostructures. The mask is typically made of a durable material, such as aluminum, that is lithographed to create at least one channel 402 that spans the depth of the mask. The channel 402 selectively permits the passage of a variety of nanostructures such as carbon nanotubes, nanotubes, nanowires, and/or nanoparticles. The dimensions of the mask 402 allow specific nanotube patterns to be generated. The mask 402 is typically made from a material which can be reused. In general, large carpets of nanotubes can be placed on top of the mask 402 to form specific masked nanotube patterns. These may then be partially submerged into a fluid anchoring layer to mass produce nanostructure composites. A further advantage of using the mask 402 is the ability to transport the composite nanostructure with the mask and original growing substrate attached. This serves to fully protect the nanostructures in commercial applications, during handling, as well as shipping.

In FIG. 4B a surface 404 having a plurality of nanostructures 412 perpendicularly orientated to the surface 404 is shown. Since the nanostructures 412 have a length that exceeds the depth of the mask 400, superimposing the surface 404 onto the mask 400 allows the plurality of nanostructures 412 associated with the surface 404 to selectively pass through the channels 402 of the mask 400. Although some of the nanostructures 406 are able to pass through the channels 402, others 408 are deflected. The nanostructures that cannot pass through the channels 402 of the mask 400 (the deflected nanostructures 408) are deflected in various directions. The nanotubes that are allowed to pass through each channel 402 allow an array of passed-though (conducted) nanostructures 406 to form a masked nanotube pattern.

Next, the passed-through nanostructures 406 are submerged in a primary fluid layer 410 at a depth, typically equal to the depth of the mask 400. The mask 400 generally prevents the deflected nanostructures 408 from entering the primary fluid layer 410. By curing or altering the primary fluid layer 410, a first anchoring structure is formed which securely fastens the passes-through nanostructures 406 to the first anchoring structure. The surface 404 may then be removed, resulting in initial composite containing nanostructures having nanostructures arranged in a masked nanotube pattern which corresponds to the channel dimensions and placement. At this point, a second primary fluid layer of the same or a different material can be applied to the first layer and then cured such that the composite heights are less than the total length of the nanostructures.

Upon generation of the nanostructure composite formed with the masked pattern, a second surface containing a second plurality of nanostructures may be immersed into a second primary fluid layer that is flowed over the previously created anchoring structure. Upon curing the second primary fluid layer, the second surface can be removed resulting in a composite containing nanostructures from multiple surfaces. Though not explicitly stated above, it is possible that a second mask may be used at this stage to create an additional nanostructure pattern. It is important to note that the height of the second fluid layer should be less than the height of the exposed portions of the nanostructures from the first surface. It should be noted that the method of spin-coating the fluid layers is one example of a method to apply the primary fluid layers evenly before they are cured.

(3) NANOSTRUCTURE COMPOSITES USING CARBON NANOTUBES

Although nanostructure composites may be formed using a variety of nanostructures and anchoring materials, the following discussion provides a detailed description of the formation of one such composite, specifically a carbon nanotube (CNT) composite.

The CNT arrays used to demonstrate the present anchoring method were grown by the well-known process of thermal Chemical Vapor Deposition on iron sputtered quartz surfaces. This growth process results in densely packed arrays of multi-walled carbon nanotubes wherever catalyst material is present. The CNT arrays are typically oriented perpendicular to the growth surface. The overall height of the array on a given sample is typically quite uniform. Overall alignment is substantially uniform at larger length scales, while entanglement is typically present at the nanoscale. The typical carbon nanotube diameter is roughly 20 nm while inter-nanotube spacing is between 50-100 nm.

Depending on the existing growth parameters such as growth time, feedgas flowrate (and therefore average flow velocity at the sample surface) and composition, system pressure, and thickness of the pre-deposited catalyst layer, array heights can be obtained on the order of 10 nm for short duration growth times but may reach over 150 nm for growth times of longer duration. In general the properties of alignment and array height uniformity tend to be more uniform for taller arrays.

Three acts of the present method include spin-coating at least one layer of uncured material to produce the desired thickness of a primary fluid layer, vertical insertion of the CNTs (or any other suitable nanostructure) into the primary fluid layer, and curing the entire assembly. The above-referenced steps may be executed any number of times in order to generate multi-layered composites, or composites having particular CNT array configurations. Optional steps such as the removal of the original growth substrate of the carbon nanotubes may also be conducted.

This present method provides straightforward control over the depth of immersion of the carbon nanotubes within the anchoring structure as well as the configuration of the anchoring structure itself. As such, a length of at least one end of the carbon nanotube may protrude out from the surface of the anchoring structure or other portions may be exposed. Freestanding flexible composite films of elastomer and protruding CNT arrays can be obtained by peeling off the films from their substrate, whereby they can be transferred to a separate surface or device component, eliminating the need for substrate and mounting surfaces as well as device components to be compatible with CNT fabrication processes.

The anchoring of carbon nanotube arrays improves handling during additional post-fabrication acts. Overall the present product provides robustness against accidental scraping, air blown or fluid flow rinse off and removal from the surface of a functional device. Importantly, patterns and local configurations of the original, as-grown carbon, nanotubes are preserved during the anchoring process. As such the present method is compatible with standard carbon nanotube growth patterning protocols.

Figure 5B:
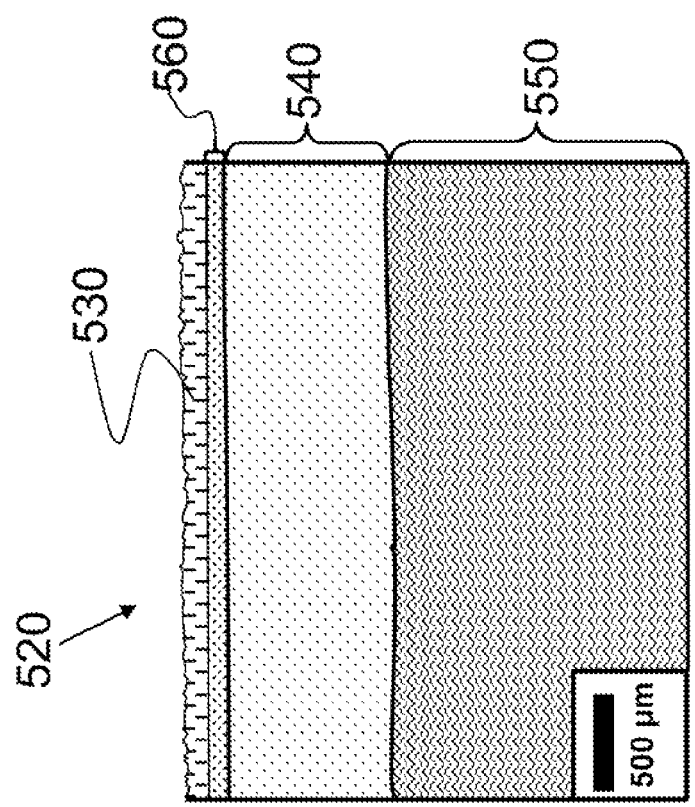
FIG. 5B is a decreased magnification cross-section illustration of a carbon nanotube composite.
Figure 5A:
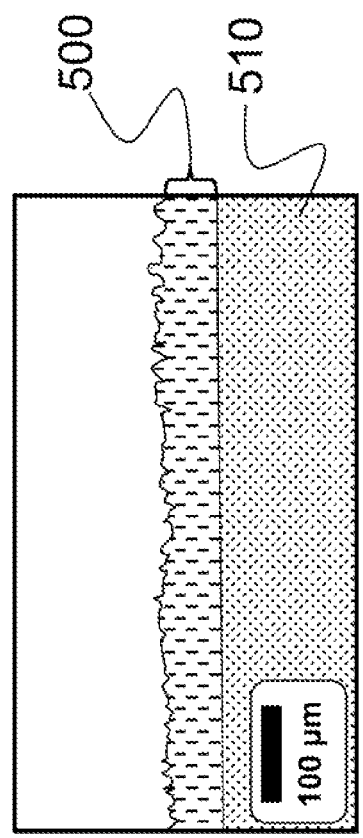
FIG. 5A is a low-magnification illustration of a 46 µm tall nanocarpet 500 anchored within an anchoring structure.

In FIG. 5A, a low magnification illustration of a 46 μm tall nanocarpet 500 anchored within an anchoring layer 510 is shown. The carbon nanotubes have been grown to form the dense nanocarpet 500. The anchoring layer 510 is a polymer plus a cross-linker composed primarily of polydimethylsiloxane (PDMS) and a platinum-containing catalyst involved in the cross linking reaction. The anchoring layer 510 is altered from a fluid to an anchoring layer (structure) 510 by actively applying heat or passively through the passage time cure. Either method results in the transformation of the polymer to a transparent silicone rubber.

In FIG. 5B, a decreased magnification cross-section illustration of the carbon nanotube composite 520 is shown. The composite 520 is comprised of the 46 μm tall nanocarpet 530 fastened within a second silicone rubber anchoring structure 560. Using scanning electron microscopy, the second silicone rubber anchoring structure 560 was measured to be roughly 29 μm thick. Prior to altering the second anchoring structure 560 with the nanocarpet 530 therein, the primary anchoring structure 540 was applied to the glass slide 550 and altered. The thick primary anchoring structure 540 had a measured thickness of 630 μm. Once the nanocarpet 520 was surrounded by the silicone fluid layer, the silicone fluid layer was altered to form the transparent anchoring structure 540 shown. Two approaches are now presented for anchoring a nanocarpet into a Room Temperature Vulcanizing (RTV) material layer.

In FIG. 6A the first approach of forming a thin layer composite 610 is shown. The thin layer composite 610 begins as a carbon nanotube array 600 attached with a supporting surface 602. The supporting surface 602 attached with the carbon nanotube array 600 is inverted, and then inserted vertically into the primary fluid layer 604. Inversion of the as-grown carbon nanotube array 600, which is inherent to the present method, may have additional benefits, since it is well-known that carbon nanotube arrays 600 are grown on a surface 602 and typically have closed ends as their tips or may also house catalyst particles. In general, for applications such as field emission and sensing, open ends are preferable, which inversion provides. The primary fluid layer 604, which surrounds the carbon nanotube array 600, is comprised of uncured RTV material which is spin-coated onto a glass slide 606. The primary fluid layer 604 is altered by exposing the entire assembly to approximately 80 C heat 608, thus forming an anchoring structure 612. The anchoring structure 612 fastens the carbon nanotube array 600 within the anchoring structure 612 at the user-specified depth and thus forms the carbon nanotube composite with carbon nanotubes 600 affixed within the anchoring structure 612. Optionally the attached supporting surface 602 may be removed from the carbon nanotube array 600. For applications in which the carbon nanotube composites in the anchoring structure 612 are further processed, handled, or shipped it is often best to abstain from removing the supporting surface 602 until necessary.

In FIG. 6B a second approach of forming a relatively thick layer carbon nanotube composite is shown. A first primary fluid layer 616 of RTV material is first created on a piece of Teflon material 614. The first primary fluid layer 616 is altered using an 80 C heat treatment 618. Once altered (or cured), the first primary fluid layer 616 becomes a first anchoring structure 620. A deposition of a second primary fluid layer 622 of uncured RTV is then placed on top of the first anchoring structure 620. A supporting surface 602' holding a carbon nanotube array 600' may then be inverted and partially immersed within the second primary fluid layer 622. The entire assembly is then heat cured 618' to form a single continuous anchoring structure 620'. The resulting "thick-on-thin" composite 624 is shown with the carbon nanostructure array 600' securely fastened within the newly formed two layered anchoring structure 620'. Because the thick primary fluid layer 616 was cured 618 first, the carbon nanotube array 600' was partially submerged to a user-specified depth within the uncured second primary fluid layer 622 deposited on top of the first anchoring structure 620. Since they were composed of the same RTV material, the first and second anchoring structures ensured good bonding at the interface between the two layers. Cured RTV does not adhere well to Teflon 614, which allows for easy release of the carbon nanotube composite 624. Optionally the attached supporting surface 602' may be removed from the carbon nanotube array 600'.

Figure 7B:
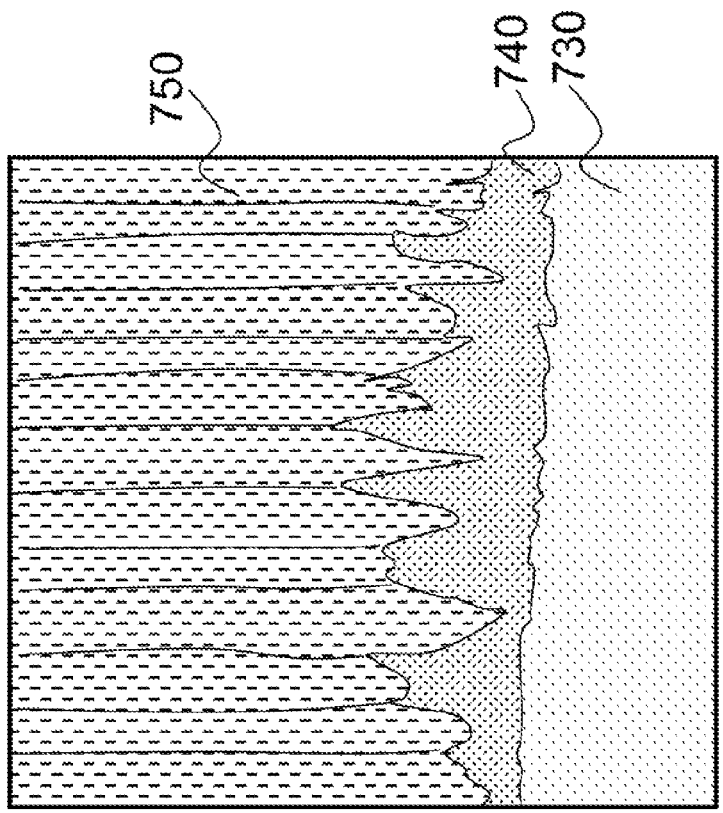
FIG. 7B is an illustration of a double anchoring structure carbon nanotube composite.
Figure 7A:
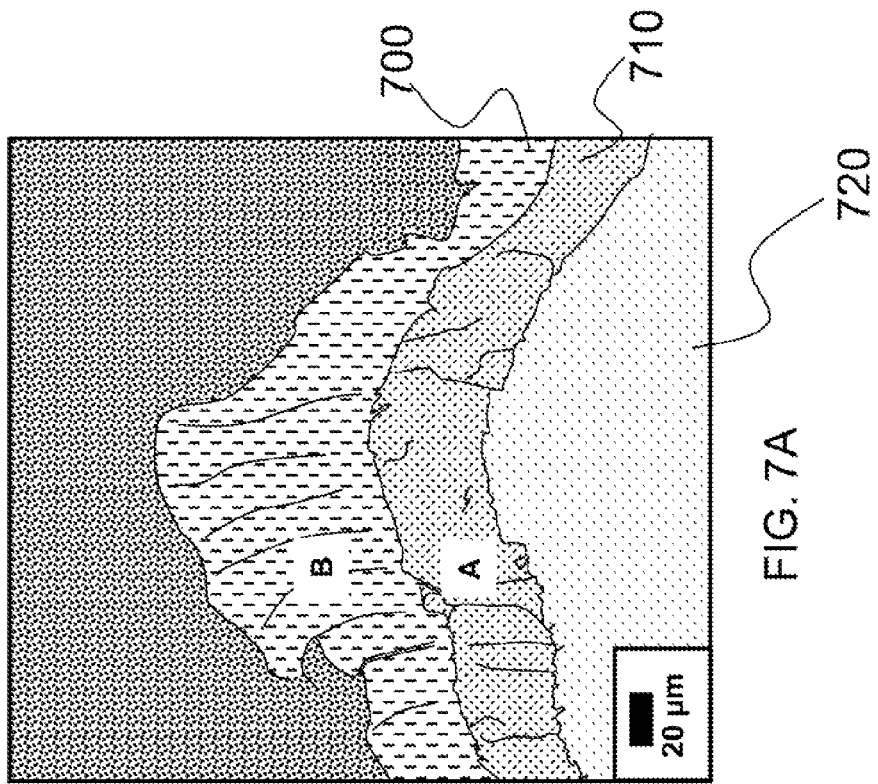
FIG. 7A is an illustration of a single anchoring structure carbon nanotube composite.

In FIG. 7A, an illustration of a cross-section of the sample, shown at a 60 degree off-vertical tilt angle is shown. A indicates the RTV anchoring layer, which is 30 μm thick at this location when corrected for viewing perspective, and B indicates the protruding, RTV material-free portion of the carbon nanotube 700 which is about 64 μm thick at this location when corrected for perspective. The scale bar is 20 μm. After spin-coating, the carbon nanotube array 700 is carefully inserted into the spun, uncured RTV primary fluid layer by inverting the carbon nanotube array 700 without contacting the carbon nanotubes comprising the array 700, and gently inserting the carbon nanotube array 700 into the fluid layer. No additional force is applied to the growth substrate 720 backside. The entire assembly composed of the glass slide, uncured RTV layer, nanocarpet, and growth substrate (and also the Teflon piece and double-stick tape, if used) was baked at approximately 80 C overnight. Following baking, the quartz growth substrate may be easily removed by gripping the sides using tweezers and lifting the substrate piece directly upward, releasing it from the carbon nanotube array 700 now implanted in the anchoring structure 710.

A small portion of the RTV material was applied to the center of the secured glass slide, and spun at 2700 rpm for 2 minutes, spreading the uncured RTV material into a thin film on the glass slide. For the thin layer sample, made without the Teflon piece, sections of the cured RTV layer, far away from the carbon nanotube array 700 implanted region, were partially released and peeled up from the glass slide using a razor and tweezers. The thickness of the RTV anchoring structure 710 was measured to be 36 μm (±2.5 μm) using a vernier thickness gauge, providing an average measurement over the gauge face area of 0.28 cm². This thickness was later confirmed in a specific location using scanning electron microscopy (SEM). The final result is shown in the lower portion of FIG. 7A. For the thin-on-thick layer sample made using the Teflon piece, the thickness of the first, thick layer of RTV material was 630 µm, measured by optical microscopy, and the thickness of the second, thin layer of RTV material into which the nanocarpet was anchored was 26 µm measured by SEM. This sample is shown in the lower part of FIG. 2 and in FIG. 3.

In FIG. 7B, an illustration showing the 51 µm thick nanocarpet 750 protruding from the 26 µm thick second anchoring structure 740, the carbon nanotube array 750 being partially anchored within the second anchoring structure 740 is shown. The carbon nanotube array 750 is anchored in the second RTV anchoring structure 740 deposited on an already cured first RTV anchoring structure 730. The second anchoring structure 740 is easily visible compared to the thick first RTV anchoring structure 730 underneath due to the high volume fraction of conductive carbon nanotube array 750 sufficiently disperses the charge from the incident electron beam, while the first anchoring structure 730 has no carbon nanotubes and is accumulating the charge, resulting in the low contrast shown.

The RTV anchoring structure 740 and 750 are comprised of PDMS and cross-linking agents. Just prior to use, the two components of the uncured RTV material were mixed by manual stirring at the manufacturer recommended 10:1 ratio by weight. A glass slide was first rinsed with isopropanol (IPA) and 18.2 MΩ-cm dionized water, dried with nitrogen, and secured to the bottom of a petri dish using double-stick tape. In the thin-on-thick layer approach, a 1/32 inch thick piece of Teflon material, which had also first been rinsed with isopropanol (IPA) and 18.2 MΩ-cm dionized water rinsed and nitrogen dried, was utilized to allow easy release of the RTV material once the final cure was completed. A large quantity of uncured RTV material mixture was spread over the Teflon surface, then baked at approximately 80 C. A final thin layer was then spun at 2700 rpm for two minutes on top of the thick, cured layer still resting on the Teflon surface, followed by nanocarpet insertion and a final bake.

Figure 8A:
FIG. 8A is an illustration of a carbon nanostructure composite showing the carbon nanostructure array at an angle with respect to the growing substrate.

In FIG. 8A a carbon nanostructure composite 800 comprised of a carbon nanostructure array 820 partially submerged within an anchoring structure 810 is shown. The carbon nanostructure array 820 forms an angle with respect to the anchoring structure 810. Although the direction of the individual nanostructures within the anchoring structure 810 is difficult to see in FIG. 8A, a graphical representation 830 characterizes their overall angled trend. In general nanostructures which are longer in length tend to be more uniform with respect to their overall orientation. Nanostructures shorter in length, however may have more anomalies with respect to the alignment of the nanostructure array 820 as it relates to the anchoring structure 810. Nonetheless at larger scale, an overall alignment can still be discerned.

Figure 8B:
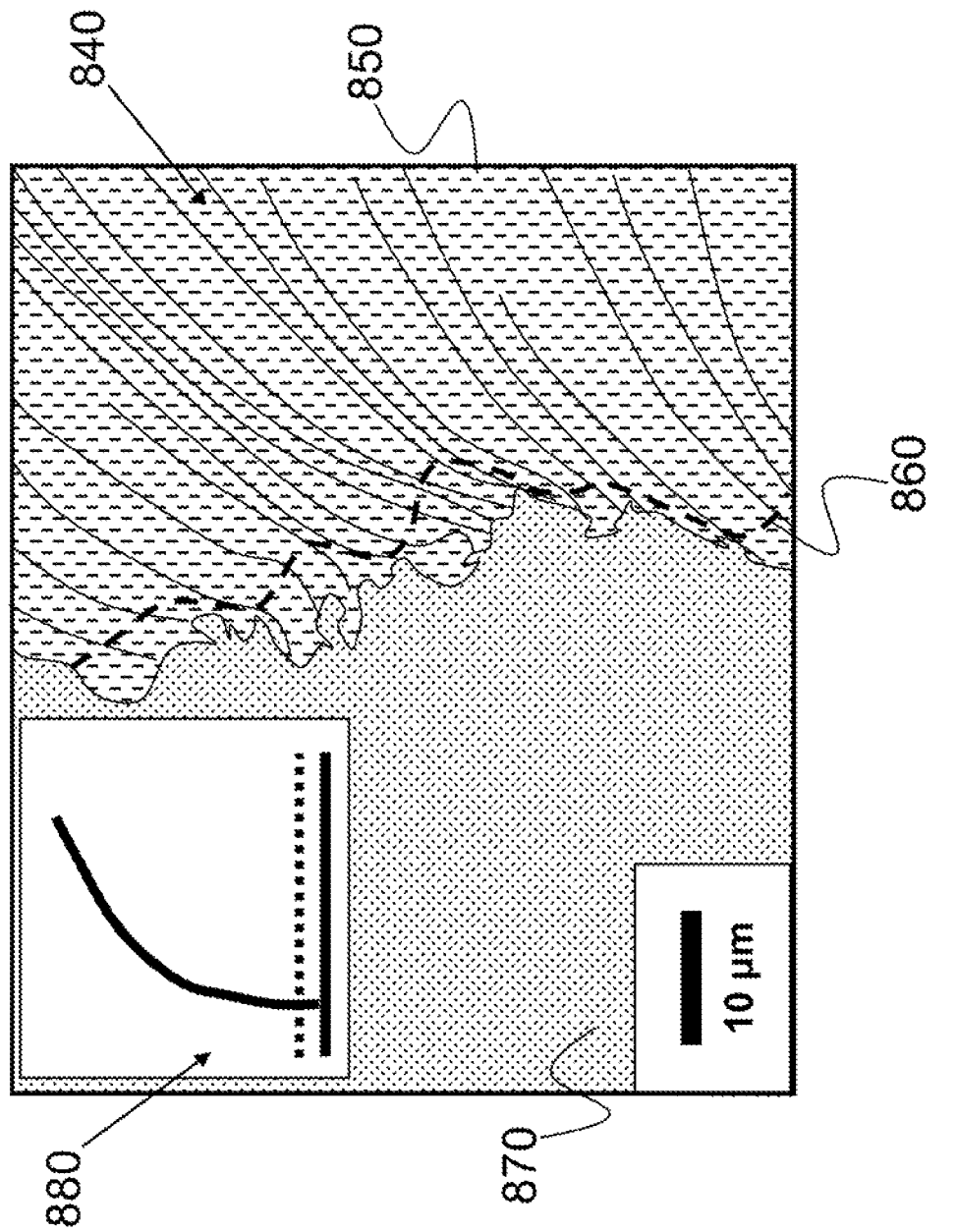
FIG. 8B is an illustration of a carbon nanostructure composite showing a carbon nanostructure composite with the carbon nanotube array substantially perpendicular to the anchoring structure.

Referring to FIG. 8B, a carbon nanostructure composite 840 comprises of a carbon nanostructure array 850 shown partially submerged within an anchoring structure 870. A boundary 860 where the carbon nanostructure array 850 and the anchoring structure 870 meet is demarcated by a dashed line. The base of the carbon nanostructure array 850 is substantially perpendicular to with respect to the anchoring structure 870. A graphical representation 880 characterizes the right angle formed at the boundary 860 which begins to tilt to one side under the weight of the nanostructure array 850.

(4) DETAILED EXPERIMENTAL PROCEDURE USING PDMS AND CROSS-LINKING AGENTS

A complete, detailed experimental procedure for carrying out the method using PDMS and cross-linking agents is listed below.

The current invention is exemplified by the following procedure, and additionally extends to other embodiments using different nanostructures to be anchored, different materials for the curable layer, and different methods of curing the materials.

Prior to Applying the Method:

A thermal CVD-grown nanocarpet was fabricated in a 1 in. diameter quartz tube furnace at approximately 725 d on a quartz substrate (1 cm×1 cm×0.16 cm) pre-coated with 5 nm Fe (sputter-coated). Feed gas was ethylene and hydrogen at 4:1 ($C_2H_4$:$H_2$) ratio, and growth time was 10 min.

Experimental Acts of the Method:

Two components of uncured RTV material (RTV615, GE Silicones, Wilton, Conn.) were mixed (10:1 ratio) by manual stirring. A small, 1½ inch diameter-sized portion was poured onto the center of a 3"51" glass slide, which was taped using double-stick tape (3M) to the bottom of a Petri dish. The Petri dish was spun for 2 minutes, spreading the viscous uncured RTV material into a thin film on the glass slide.

Following spin-coating, the growth substrate (and the nanocarpet supported on its surface) was gently placed upside down into the thin layer of uncured RTV material, inserting a portion of the nanocarpet into the RTV layer. No additional force was applied to the growth substrate's backside.

The glass slide-RTV-nanocarpet-growth substrate assembly was baked at approximately 80 C overnight (14 hours) to cure the RTV material fully.

Following baking, the growth substrate was easily removed by gently gripping the sides using tweezers and lifting the substrate piece directly upward. The growth substrate released from the nanocarpet, leaving the nanocarpet implanted in the cured RTV layer, with the previous "bottom" surface now as the upper surface.

Sections of the cured RTV layer far away from the nanocarpet implanted region were partially released and peeled up from the glass slide using a razor, and the thickness of the RTV layer was measured to be 36 µm using a vernier thickness gauge.

To test the strength and continuity of the cured RTV layer in the nanocarpet embedded region, tweezers were used to pull on a piece of anchored nanocarpet which was standing up from the surface.

Finally, the removed pieces of anchored nanocarpet and the remainder were characterized in SEM.

(5) FURTHER CONCEPTS

As previously mentioned, the primary fluid layer may comprise one fluid layer or multiple fluid layers. Cases illustrated above generally illustrate the case where the primary fluid layer includes one fluid layer. This situation is simply illustrated in FIG. 9A to FIG. 9D. In FIG. 9A, a plurality of nanostructures 900 is illustrated, grown on a growth substrate 910. In FIG. 9B a primary fluid layer 920 is formed on an anchoring substrate 930. FIG. 9C illustrates the nanostructures 900 after immersion to a desired depth in the primary fluid layer 920. Subsequently, the primary fluid layer 920 is altered to form an anchoring structure 940 and the growth substrate 910 is removed leaving the device illustrated in FIG. 9D.

The primary fluid layer can also be formed of multiple fluid layers as illustrated in FIG. 10 and FIG. 11. FIG. 10A to FIG. 10E illustrate a case where the primary fluid layer comprises two fluid layers. In this case, one of the fluid layers either does not alter during the altering act or does alter, but is easily removed, resulting in a device with nanotubes protruding through both sides. In particular, FIG. 10A illustrates a plurality of nanostructures 1000 grown on a growth substrate 1010. A primary fluid layer 1020 comprising a first fluid layer 1020' and a second fluid layer 1020" is formed on an anchoring substrate 1030 as illustrated in FIG. 10B. Typically, the fluid layer is formed by spin-coating. The fluids may be formed by sequential spin-coating operations. The fluids may also be spin-coated together and may separate/stratify by a property such as pressure, density, viscosity, immiscibility, and phobicity. The nanotubes 1000 are introduced into the primary fluid layer 1020 to a desired depth. As illustrated in FIG. 10C, at least one of the fluid layers 1020' and 1020" is then altered to form an anchoring structure 1040 comprising layers 1040' and 1040" and the growth substrate 1010 is removed as illustrated in FIG. 10D. Next, one of the layers 1040' is removed leaving the nanostructures 1000 embedded in what is left of the anchoring structure 1040 as illustrated in FIG. 10E. As previously stated, the removed layer 1040' may be formed of a material that does not alter when the other layer does (e.g., water when the other layer is a polymer). It may also be formed of a material that does alter, but that adheres very loosely to the nanostructures and the other layer (e.g., wax when the other layer is a polymer). Additionally, the removed layer 1040' may be formed of a material that alters, but that may be removed by re-altering the material (e.g., wax that is cooled to solidify when the other layer is a polymer, where the wax can be re-heated and removed when in liquid form). In this case, removal of layer 1040' results in the removal of the anchoring substrate 1030.

A more complex situation is illustrated in FIG. 11, where several fluid layers are incorporated. As shown in FIG. 11A, a plurality of nanostructures 1100 are grown on a growth substrate 1110. A primary fluid layer 1120 comprised of fluid layers 1120', 1120", 1120''', and 1120"" is formed on an anchoring substrate 1130 as illustrated in FIG. 11B. The nanostructures 1100 are introduced to a desired depth in the primary fluid layer 1120 as illustrated in FIG. 11C. Ones of the fluid layers 1120', 1120", 1120''', and 1120"" are altered to form an anchoring structure 1140 comprising layers 1140', 1140", 1140''', and 1140"" and the growth substrate 1110 is removed as illustrated in FIG. 11D. Next, the unaltered fluid layers are removed leaving the nanostructures 1100 embedded in what is left of the anchoring structure 1140 as illustrated in FIG. 11E. In this case, removal of layer 1140' results in the removal of the anchoring substrate 1130.

Another concept that may be employed is presented in FIG. 12, where the nanostructures 1200 are grown in nanostructure cells 1210. As shown in FIG. 12A, the nanostructure cells 1210 have heights/depths 1220. The nanostructures 1200 are grown such that they extend beyond the nanostructure cells 1210. FIG. 12B, illustrates a situation where the nanostructure cells 1210 have varying heights/depths 1220, which permits controlled variation of the length by which the nanostructures 1200 extend beyond the fluid layer when immersed. The varying heights/depths 1220 can be patterned as desired. FIG. 12C illustrates a plurality of nanostructures 1200 immersed in a primary fluid layer 1230 on an anchoring substrate 1240 to a depth where the nanostructure cells 1220 just contact the fluid layer 1230. FIG. 12D illustrates a top view of the nanostructure cells 1210. Although the nanostructure cells 1210 are depicted as pentagons they may be any shape as desired or as useful for a particular embodiment. Further, the nanostructure cells 1210 may be distributed continuously or non-continuously across the growth substrate.

Figure 13A:
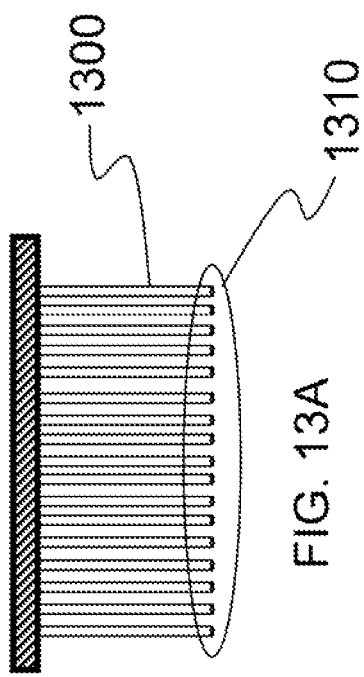
FIG. 13A is a side view illustration showing a plurality of nanostructures grown on a growth substrate, where the tips of the nanostructures are coated with a material or encased in a bubble.
Figure 13B:
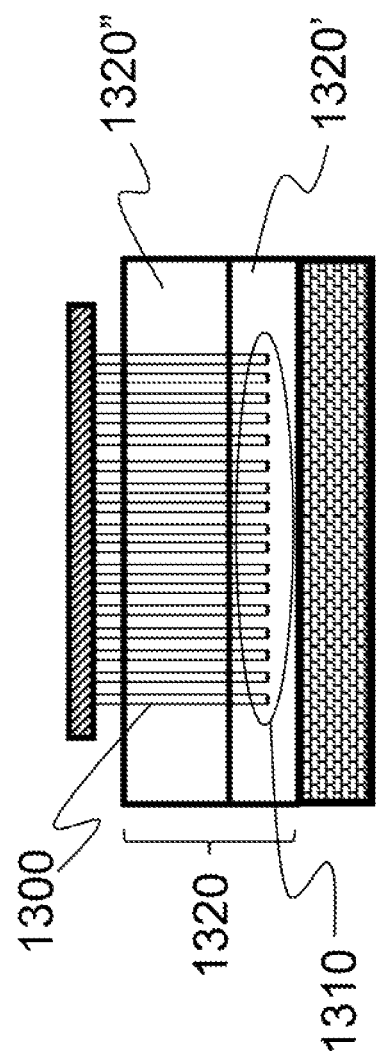
FIG. 13B is a side view illustration showing a plurality of nanostructures after immersion in a primary fluid layer, where the primary fluid layer comprises of two fluid layers and where the tips of the nanostructures are coated with a material or encased in a bubble.

As a further concept, as illustrated in FIG. 13A, nanostructures 1300 may be coated with a material or a bubble may be formed around the nanostructure tips to facilitate removal of fluid layer 1320'. In the specific case of FIG. 13, a bubble 1310 is illustrated. The bubble 1310 may be formed of various materials such as thin glass, etc. This allows for the nanostructures to be protected during the removal process since fluid layer 1320' will have little contact with the nanostructure. In FIG. 13B nanostructures 1300 are illustrated immersed in a primary fluid layer 1320 comprising a first fluid layer 1320' and a second fluid layer 1320". An additional benefit of the material or bubble is that it helps keep the nanostructure tips free from the material comprising the primary fluid layer 1320 so that after the primary fluid layer 1320 is altered, the tips of the nanostructures 1300 are clean and free of leftover altered fluid layer material.

Two additional, related manufacturing techniques are shown in FIG. 14 and FIG. 15. It should be appreciated that both techniques are shown as cross-sections of shapes that could be tubular in nature, shell-like structures, or other, more irregular in nature. Additionally, although the cross-sections FIG. 14 and FIG. 15 are depicted with circular and hexagonal cross-sections, respectively, these are intended to be exemplary only, and can be varied according to the needs of an actual device. Further, both cross-sections in FIG. 14 and FIG. 15 are shown as closed shapes. Again, this is intended to be an exemplary feature and may be varied according to the needs of an actual device. Finally, the primary fluid layers depicted in FIG. 14 is shown with a single layer and that in FIG. 15 is shown with two layers. Depending on the particular application, the actual primary fluid layer may comprise either a single layer or a plurality of fluid layers. Finally, in both techniques, the relative positions of the growth substrate/ nanostructures and the anchoring substrate/primary fluid layer may be interchanged as desired.

Figure 14B:
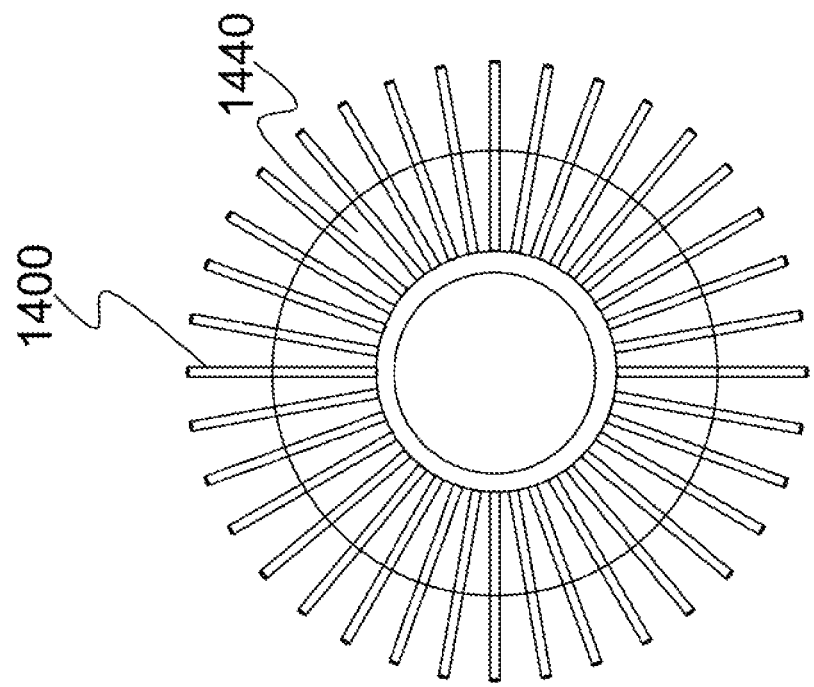
FIG. 14B is a side view illustration showing a plurality of nanostructures partially embedded within an anchoring structure.
Figure 14A:
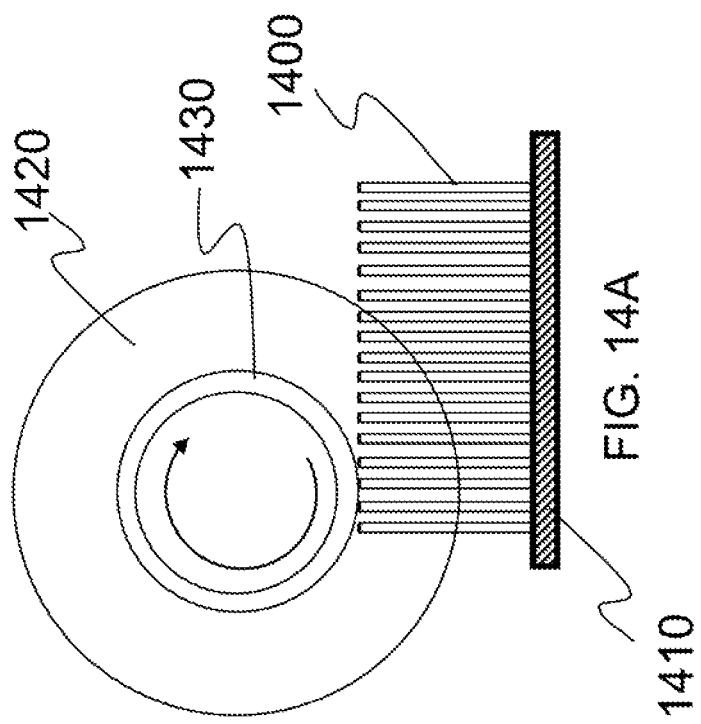
FIG. 14A is a side view illustration showing a plurality of nanostructures being introduced into a primary fluid layer, where a growth substrate and an anchoring layer are moved relative to each other to introduce the nanostructures into the primary fluid layer.

Referring now to FIG. 14A, a plurality of nanostructures 1400 on a growth substrate 1410 are introduced into a primary fluid layer 1420 on an anchoring substrate 1430. In this case, the growth substrate 1410 and the anchoring substrate 1430 are moved relative to each other (for example, the anchoring substrate 1430 may be rotated and moved relative to the growth substrate 1410), thus introducing the nanostructures 1400 into the primary fluid layer 1420. As this movement occurs, the primary fluid layer 1420 is altered to form an anchoring structure 1440, as shown in FIG. 14B, having a plurality of nanostructures 1400 embedded therein. Alternatively, the primary fluid layer 1420 may be a semi-solid pickup layer that has sufficient viscosity to remove the nanostructures 1400 from the growth substrate 1410. In this case, the primary fluid layer 1420 may be altered to form the anchoring structure 1440 at a later time.

With respect to FIG. 15A, a plurality of nanostructures 1500 is shown on a hexagonal growth substrate 1510. An inflatable anchoring substrate 1520 having a primary fluid layer 1530 thereon, resides within the growth substrate 1510. The primary fluid layer 1530 comprises a first fluid layer 1540 and a second fluid layer 1550. Pressure 1560 is used to expand the anchoring substrate 1520 so that the nanostructures 1500 are introduced to a desired depth in the primary fluid layer 1530. At least a portion of the primary fluid layer 1530 is then altered to form an anchoring structure 1570, as shown in FIG.

15B, having a plurality of nanostructures embedded therein. In the case shown, the (either cured or uncured, depending on the particular embodiment) second fluid layer 1550 is removed, with the altered first fluid layer 1540 forming the anchoring structure 1570.

With respect to the method of FIG. 15, depending on the pressure applied, the end anchoring structure 1570 may take the inner shape of the growth substrate 1510, or its edges may be more rounded. Also, as would be appreciated by one of skill in the art, the pressure 1560 may be pneumatic, hydraulic, mechanical, or other. Additionally, in other embodiments, the pressure may also be applied to the growth substrate 1510.

The methods shown in FIG. 14 and FIG. 15 can be used with various primary fluid layer altering techniques such as hot embossing.

(6) APPLICATIONS

Devices of the present invention have a wide variety of applications in a range of fields. Non-limiting examples of such applications are listed below by field.

Medical/Bio-Technology

Medical applications include uses such as eye patches (e.g., synovial eye patches for medicine delivery to aid in cases of near retina sclera and macular degeneration), colon cancer treatments, $Z^3$ dermatology, angioplasty devices. In such devices, drugs can be introduced to the nanostructures by taking advantage of hydrophobic/hydrophilic properties of certain medicine solutions and the nanotubes act as a set of nano-needles to penetrate tissues for drug delivery. The properties of particular drugs may be tailored to adjust their hydrophobic/hydrophilic properties to optimize pickup by particular nanostructure materials (e.g., carbon in the case of carbon nanotubes).

Further, devices according to the present invention can be used in other medical/bio-technology applications such as gene delivery, cell assays, dialysis treatments, and bio-marker cancer screening.

Energy

Energy applications (particularly for cases where the nanostructures have ends extending from each side of the anchoring structure) include solar thermal energy collection for both terrestrial and space-based applications, heat transfer (heat exchangers) for conductive heat transfer and convective microfluidic heat transfer. Applications include both heating and refrigeration. In heat exchanger applications, the nanotubes provide for greater surface areas for conduction.

Fluid Purification

In cases where the nanostructures have ends extending from each side of the anchoring structure, devices of the present invention can act as microfluidic water (or other liquid) filters and gas/air particulate filters.

Miscellaneous

Taking advantage of electrical properties, in cases where the nanostructures have ends extending from each side of the anchoring structure, devices of the present invention (with an applied current) can act as self-cleaning surfaces. Further, the nanotubes can be selected for characteristics that allow for drag reduction/increase in the characteristics of passing fluids. This property has uses in many fluid flow situations from piping to ship-building.

It should be noted that the above applications are just a few examples of the set of possible applications for devices of the present invention. In addition, these applications may be combined as desired. For example, in the case of a device where the nanostructures have ends extending from each side of the anchoring structure, it may be used as an air filter that when dirty, may be cleaned/renewed by acting as a self-cleaning surface through the application of a current.

(7) CONCLUSION

The nature of the anchored nanostructures and the anchoring materials produced by the method of the present invention depend on the properties of the curable fluid, including flexibility, strength, and hardness in the cured state, optical transparency in the cured state, and viscosity, density, and nanostructure wettability in the uncured state.

Similarly part of the nature of the anchored nanostructures and anchoring material produced by the method of the current invention depends on the thickness of the uncured primary fluid layer into which the nanostructures are inserted, resulting in control over the portion of the total length of nanostructures which protrudes from the cured material. The length of nanostructures protruding from the anchoring structure may be given by the total length of the nanostructure minus the thickness of the primary fluid layer into which the nanostructures are inserted.

As previously mentioned, the present invention is applicable in diverse applications in many fields, such as surface actuators, ultra-high surface area super-capacitors, electrostatically actuated surfaces, hydrodynamic drag reduction, field emission devices, transparent flexible electronics and displays, heat transfer and thermal radiators, micro-templates for biological cell growth and tissue culture, controlled active and passive fluid transport for lab-on-a-chip, and optically active surfaces. All of these in some way require a portion of the nanostructures to be free and protruding from the anchoring material, rather than fully embedded within it, in order to take advantage of the functionality of the nanostructures and allow them to be manipulated and otherwise interact with their environment.

The present invention is still further directed to a method of bringing together large numbers of pre-fabricated nanostructures and a curable material in which the preformatted nanostructures are to be anchored to a specified depth by being held at their base by the cured material when it is in its final state. This method has the very important feature of leaving a specified portion of the total original length of the nanostructures protruding from the anchoring material, and therefore available for interaction with the environment and retaining any advantageous inherent function of the nanostructures.

Figure 16B:
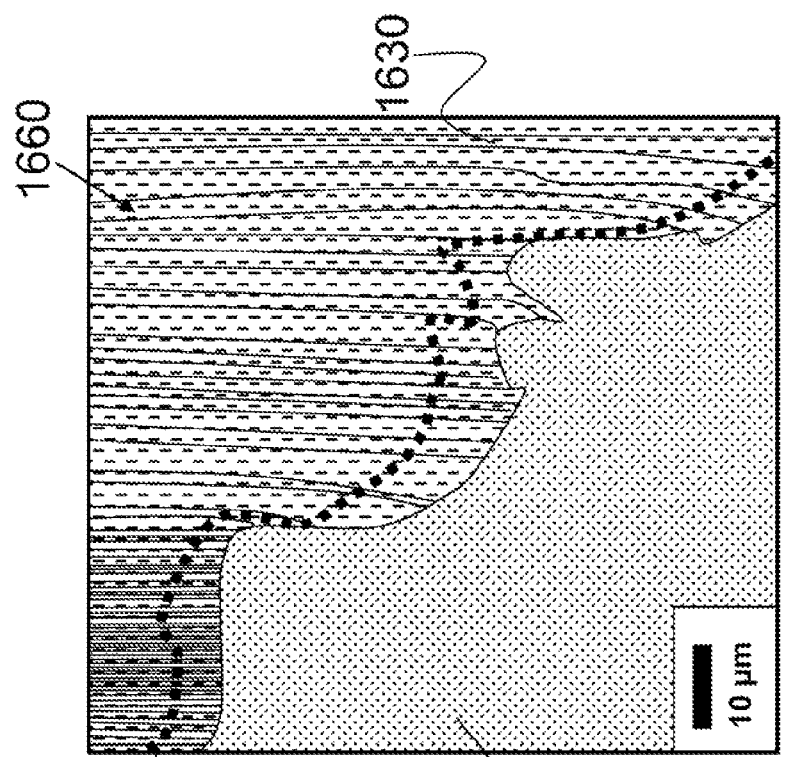
FIG. 16B is an illustration of an anchored carbon nanotube array.
Figure 16A:
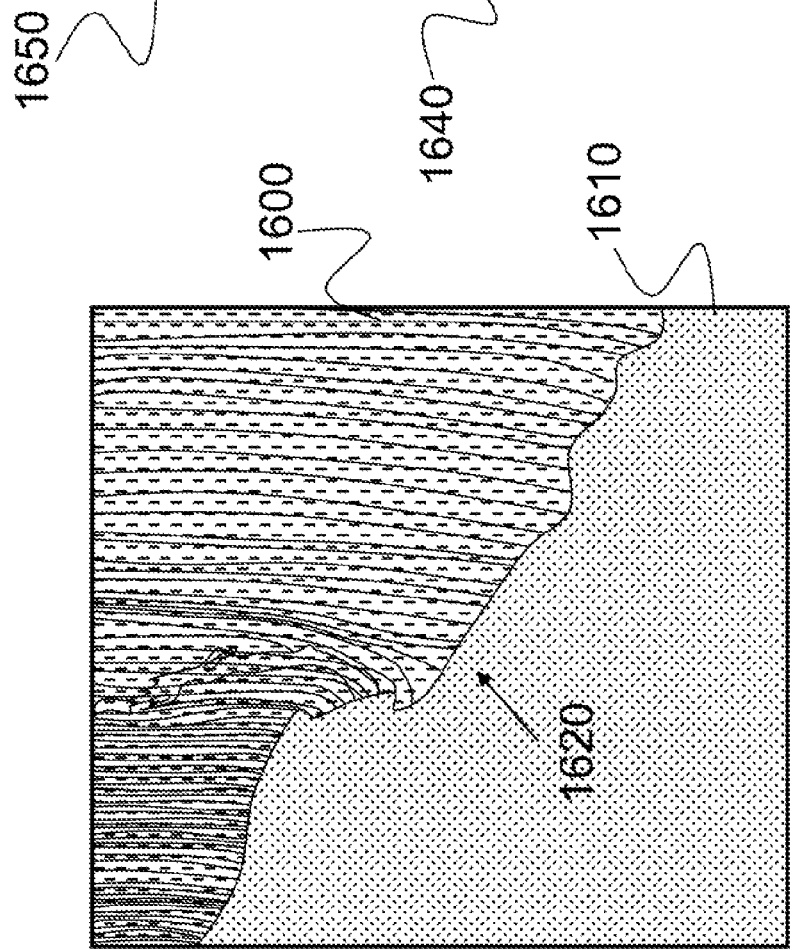
FIG. 16A is an illustration of an unanchored carbon nanotube array.

Referring to FIG. 16A, an illustration of an unanchored carbon nanotube array 1600 is shown. The carbon nanotube array 1600 resides on a growth substrate 1610. The junction 1620 between the growing substrate 1610 and the carbon nanotube array 1600 is pronounced. PMMA is used as the anchoring material to form the carbon nanotube composite 1660 shown in FIG. 16B. By inverting the carbon nanotube array 1600, the invented carbon nanotube array 1630 may then be immersed and surrounded by a primary fluid layer. By curing the PMMA, a carbon nanotube composite 1660 is formed.

Anchoring the carbon nanotube array 1630 has an effect on the mechanical properties of the array. The carbon nanotube array 1630 is held within the anchoring structure 1640. The altered mechanics arise in part due to the anchoring of carbon nanotube array 1630, but primarily as a byproduct of producing the carbon nanotube composite 1660.

In order to verify that the carbon nanotubes 1630 are firmly anchored within the anchoring structure 1640, a friction drag reduction experiment was conducted. The carbon nanotube composite 1660 was placed in a 5.5 m/s water jet impinging the carbon nanotube composite 1660 at a 45 degree angle.

This experiment was designed to create a realistic wall shear stress on the anchored carbon nanotube composite 1660, similar to that expected for full-size ships at moderate speeds (10 knots). Though real watercraft may experience turbulent boundary layer flows at length-based Reynolds numbers of up to 1010, a power-law fit to measured wall shear stress data obtained from a turbulent boundary layer with length-based Reynolds numbers of up to $2.1 \times 10^8$ predicts a wall shear stress of between 260 and 440 dynes/cm$^2$ for 6 m/s free stream velocity. The wall shear stress caused by the 5.5 m/s impinging water jet was estimated to be 230 dynes/cm$^2$ using the classical. Hiemenz flow solution for a plane stagnation flow. The optical micrographs along with visual observation, clearly indicated that no regions of the carbon nanotube composite 1660 were removed from the anchoring structure 1640 in which they were anchored. Thus, even at realistic levels of wall shear stress, the carbon nanotube composite 1660 and the method for producing the same displayed the ability to retain the carbon nanotubes 1630 within the anchoring structure 1640 when exposed to a substantial shearing force.

What is claimed is:

1. A method for fastening a plurality of nanoscale structures within an anchoring structure, comprising:
    providing a primary fluid layer on an anchoring substrate;
    providing a plurality of nanostructures on a growth substrate on which the nanostructures were grown, the nanostructures each having a defined height and orientation with respect to the initial substrate; and
    introducing the plurality of nanostructures to a desired depth in the primary fluid layer, such that the orientation of the nanostructures relative to the growth substrate is substantially maintained; where the primary fluid layer comprises multiple fluid layers; and where ones of the multiple fluid layers are selected such that when altered to form an anchoring structure, a portion of the anchoring structure can be removed, leaving the anchoring structure permitting exposure of at least a portion of the nanostructures.

2. A method for fastening a plurality of nanoscale structures within an anchoring structure as set forth in claim 1, where the fluid layers are selected such that when altered to form the anchoring structure a portion of the anchoring structure can be removed permitting exposure of at least a number of nanostructures through two sides of the anchoring structure.

3. A method for fastening a plurality of nanoscale structures within an anchoring structure as set forth in claim 2, further comprising altering the fluid layers to form the anchoring structure, thereby affixing at least a portion of the nanostructures within the anchoring structure, whereby the growth substrate may be removed, leaving at least a portion of the nanostructures affixed within the anchoring structure.

4. A method for fastening a plurality of nanoscale structures within an anchoring structure as set forth in claim 3, further comprising removing a portion of the anchoring structure, permitting exposure of at least a number of nanostructures through two sides of the anchoring structure.

5. A method for fastening a plurality of nanoscale structures within an anchoring structure as set forth in claim 4, removing the growth substrate to leave a set of nanostructures, where at least a portion of the set of nanostructures is affixed within the anchoring structure.

6. A method for fastening a plurality of nanoscale structures within an anchoring structure as set forth in claim 1, where the growth substrate comprises a set of nanostructure cells, the nanostructures each having a defined height and orientation with respect to the growth substrate, where the nanostructures extend beyond the nanostructure cells; and where, in the act of introducing the plurality of nanostructures to a desired depth in the primary fluid layer, the nanostructure cells are made to contact the primary fluid layer; whereby, the nanostructures extend beyond the primary fluid layer by a depth approximately equal to a depth of the nanostructure cells.

7. A method for fastening a plurality of nanoscale structures within an anchoring structure as set forth in claim 6, where the depth the nanostructure cells is selected prior to growth of the nanostructures, thereby providing varying lengths of nanostructures beyond the fluid layer.

8. A method for fastening a plurality of nanoscale structures within an anchoring structure as set forth in claim 1, where ones of the multiple fluid layers are stratified with respect to other ones of the multiple fluid layers, such that ones of the multiple fluid layers may be altered independently of others of the multiple fluid layers to form the anchoring structure; whereby the growth substrate and at least a portion of the anchoring structure may be removed to permit exposure of at least a portion of the nanostructures.

9. A method for fastening a plurality of nanoscale structures within an anchoring structure as set forth in claim 8, further comprising altering the fluid layers to form an anchoring structure, thereby affixing at least a portion of the nanostructures within the anchoring structure, whereby the growth substrate may be removed, leaving at least a portion of the nanostructures affixed within the anchoring structure.

10. A method for fastening a plurality of nanoscale structures within an anchoring structure as set forth in claim 9, further comprising removing a portion of the anchoring structure, permitting exposure of at least a portion of the nanostructures.

11. A method for fastening a plurality of nanoscale structures within an anchoring structure as set forth in claim 10, further comprising removing the growth substrate to leave a set of nanostructures, where at least a portion of the set of nanostructures is affixed within the anchoring structure.

12. A method for fastening a plurality of nanoscale structures within an anchoring structure as set forth in claim 8, where the multiple fluid layers are stratified with respect to each other by a property selected from the group of pressure, density, viscosity, immiscibility, and phobicity, and where materials for the fluid layers are selected to permit selective altering of various ones of the fluid layers to allow selected portions of the nanostructures to be anchored in various portions of the anchoring structure.

13. A method for fastening a plurality of nanoscale structures within an anchoring structure, comprising:
    providing a primary fluid layer on an anchoring substrate;
    providing a plurality of nanostructures on a growth substrate on which the nanostructures were grown, the nanostructures each having a defined height and orientation with respect to the growth substrate; and
    introducing the plurality of nanostructures to a desired depth in the primary fluid layer, such that the orientation of the nanostructures relative to the growth substrate is substantially maintained; where the primary fluid layer comprises multiple fluid layers; and where the fluid layers are selected such that when altered to form an anchoring structure a portion of the anchoring structure can be removed, permitting exposure of the nanostructures through two sides of a remainder anchoring structure.

14. A method for fastening a plurality of nanoscale structures within an anchoring structure as set forth in claim 13, further comprising altering the primary fluid layer to form an anchoring structure, thereby affixing at least a portion of the nanostructures within the anchoring structure, whereby the growth substrate may be removed, leaving at least a portion of the nanostructures affixed within the substrate.

15. A method for fastening a plurality of nanoscale structures within an anchoring structure as set forth in claim 14, further comprising removing the growth substrate to leave a set of nanostructures, where at least a portion of the nanostructures is affixed within the anchoring structure.

16. A method for fastening a plurality of nanoscale structures within an anchoring structure as set forth in claim 13, wherein the nanostructures are carbon nanotubes.

17. A method for fastening a plurality of nanoscale structures within an anchoring structure as set forth in claim 13, wherein the nanostructures are arranged in a pattern on the growth substrate.

18. A method for fastening a plurality of nanoscale structures within an anchoring structure as set forth in claim 13, where providing the anchoring structure on the anchoring substrate is accomplished by spin-coating at least a portion of the fluid layer onto the anchoring substrate to provide a substantially uniform thickness.

19. A method for fastening a plurality of nanoscale structures within an anchoring structure as set forth in claim 13, wherein the plurality of nanostructures are comprised of different materials.

20. A method for fastening a plurality of nanoscale structures within an anchoring structure, comprising:
    providing a primary fluid layer on an anchoring substrate;
    providing a plurality of nanostructures on a first anchoring structure, the nanostructures each having a defined height and orientation with respect to the first anchoring structure; and
    introducing the plurality of nanostructures to a desired depth in the primary fluid layer, such that the orientation of the nanostructures relative to the first anchoring structure is substantially maintained; where the primary fluid layer comprises multiple fluid layers; and where ones of the multiple fluid layers are selected such that when altered to form a second anchoring structure, a portion of the second anchoring structure can be removed, leaving the second anchoring structure permitting exposure of at least a portion of the nanostructures.

21. The method of claim 20, where the fluid layers are selected such that when altered to form the second anchoring structure a portion of the second anchoring structure can be removed permitting exposure of at least a number of nanostructures through two sides of the second anchoring structure.

22. The method of claim 21, further comprising altering the fluid layers to form the second anchoring structure, thereby affixing at least a portion of the nanostructures within the second anchoring structure.

23. The method of claim 22, further comprising removing a portion of the second anchoring structure, permitting exposure of at least a number of nanostructures through two sides of the second anchoring structure.

24. The method of claim 20, where ones of the multiple fluid layers are stratified with respect to other ones of the multiple fluid layers, such that ones of the multiple fluid layers may be altered independently of others of the multiple fluid layers to form the second anchoring structure; whereby the first anchoring structure and at least a portion of the second anchoring structure may be removed to permit exposure of at least a portion of the nanostructures.

25. The method of claim 24, further comprising altering the fluid layers to form the second anchoring structure, thereby affixing at least a portion of the nanostructures within the second anchoring structure.

26. The method of claim 25, further comprising removing a portion of the second anchoring structure, permitting exposure of at least a portion of the nanostructures.

27. The method of claim 25, where the multiple fluid layers are stratified with respect to each other by a property selected from the group of pressure, density, viscosity, immiscibility, and phobicity, and where materials for the fluid layers are selected to permit selective altering of various ones of the fluid layers to allow selected portions of the nanostructures to be anchored in various portions of the second anchoring structure.

\* \* \* \* \*